United States Patent
Chen et al.

(10) Patent No.: US 6,549,801 B1
(45) Date of Patent: Apr. 15, 2003

(54) PHASE-RESOLVED OPTICAL COHERENCE TOMOGRAPHY AND OPTICAL DOPPLER TOMOGRAPHY FOR IMAGING FLUID FLOW IN TISSUE WITH FAST SCANNING SPEED AND HIGH VELOCITY SENSITIVITY

(75) Inventors: Zhongping Chen; Yonghua Zhao, both of Irvine; J. Stuart Nelson, Laguna Niguel; Johannes F. DeBoer, Irvine, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/574,560

(22) Filed: May 19, 2000

Related U.S. Application Data

(63) Continuation-in-part of application No. 09/096,434, filed on Jun. 11, 1998.
(60) Provisional application No. 60/135,363, filed on May 21, 1999.

(51) Int. Cl.[7] ................................................ A61B 5/05
(52) U.S. Cl. ........................ 600/425; 600/473; 600/476; 250/363.02; 250/368; 250/350; 250/385; 250/483
(58) Field of Search ............................... 600/476, 310, 600/368, 407, 425, 473; 250/363.02, 368, 356, 385, 483

(56) References Cited

U.S. PATENT DOCUMENTS 5,991,697 A * 11/1999 Nelson et al. ................ 702/49
6,208,415 B1 * 3/2001 De Boer et al. ............. 356/351

* cited by examiner

*Primary Examiner*—Marvin M. Lateef
*Assistant Examiner*—Jeoyuh Lin
(74) *Attorney, Agent, or Firm*—Daniel L. Dawes; Myers, Dawes & Andras LLP

(57) ABSTRACT

The invention is a fast-scanning ODT system that uses phase information derived from a Hilbert transformation to increase the sensitivity of flow velocity measurements while maintaining high spatial resolution. The significant increases in scanning speed and velocity sensitivity realized by the invention make it possible to image in vivo blood flow in human skin. The method of the invention overcomes the inherent limitations of the prior art ODT by using a phase change between sequential line scans for velocity image reconstruction. The ODT signal phase or phase shifts at each pixel can be determined from the complex function, $\tilde{\Gamma}_{ODT}(t)$, which is determined through analytic continuation of the measured interference fringes function, $\Gamma_{ODT}(t)$, by use of a Hilbert transformation, by electronic phase demodulation, by optical means, or a fast Fourier transformation. The phase change in each pixel between axial-line scans is then used to calculate the Doppler frequency shift. Sequential measurements of a single line scan, measurements of sequential line scans or measurements of line scans in sequential frames may be used. Because the time between line scans is much longer than the pixel time window, very small Doppler shifts can be detected with this technique. In addition, spatial resolution and velocity sensitivity are decoupled. Furthermore, because two axial-line scans are compared at the same location, speckle modulations in the fringe signal cancel each other and, therefore, will not affect the phase-difference calculation.

42 Claims, 10 Drawing Sheets

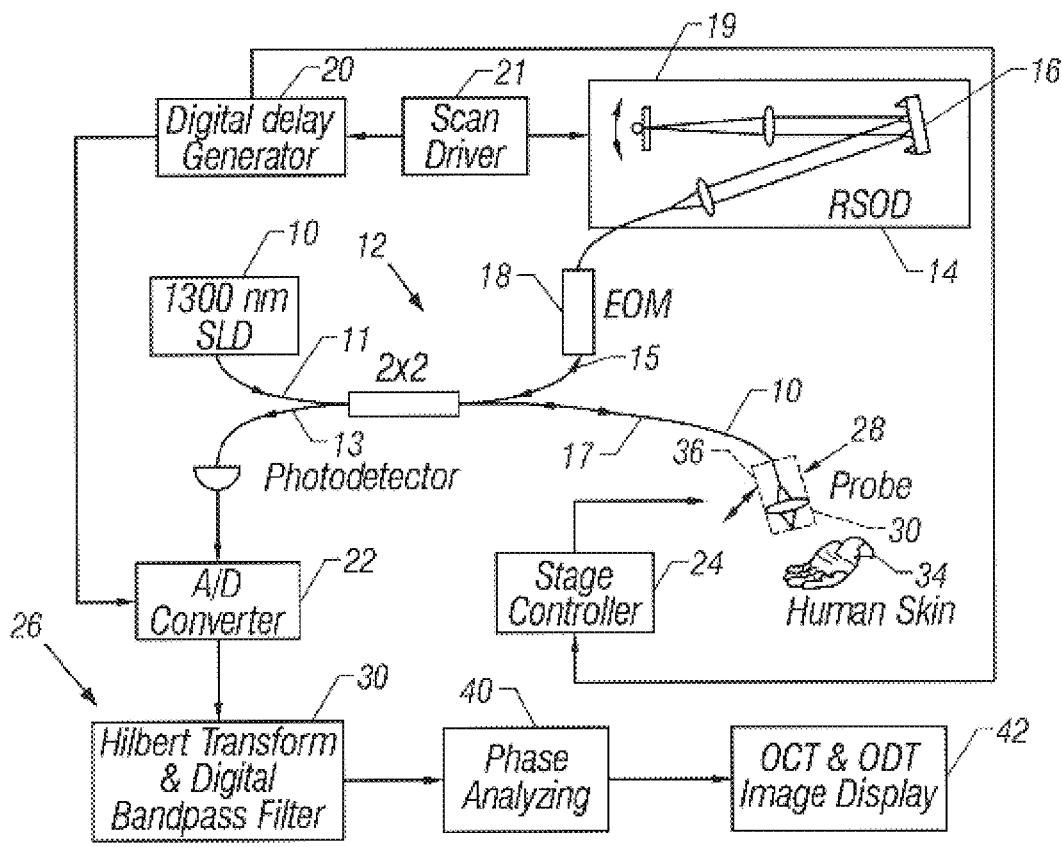
FIG. 1
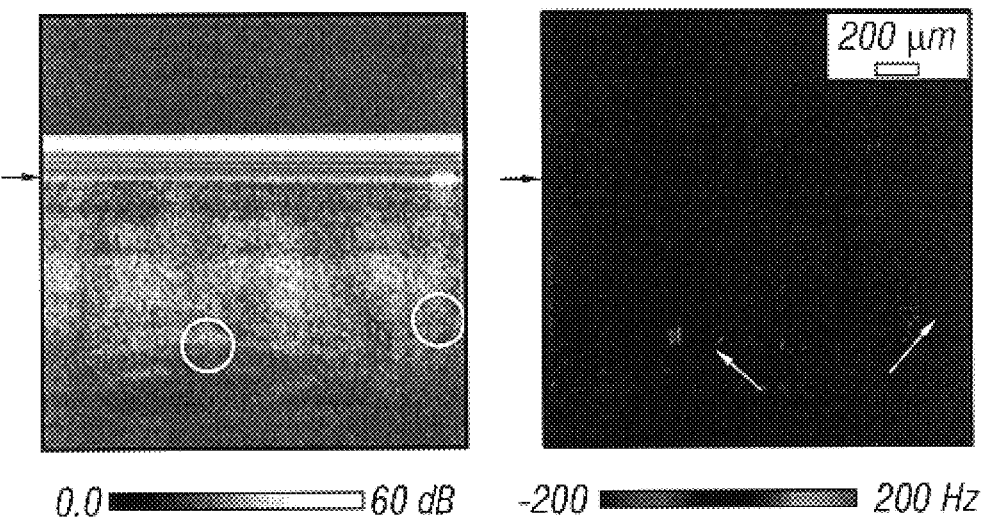
FIG. 3A  FIG. 3B

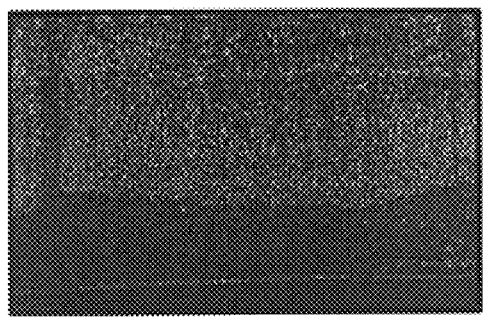
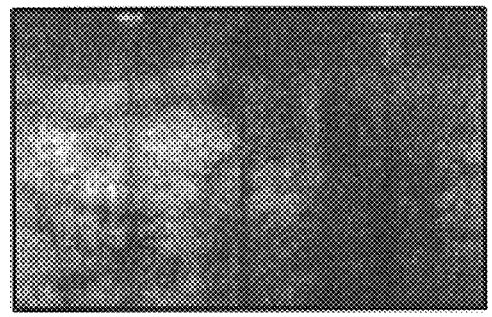
■ 250 μM    0.0 ■ 60 dB
*FIG. 5A*    *FIG. 5D*
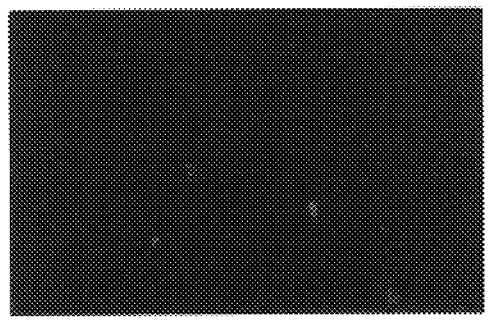
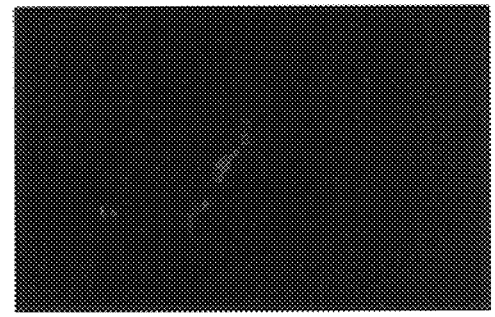
-500 ■ 500 Hz
*FIG. 5B*    *FIG. 5E*
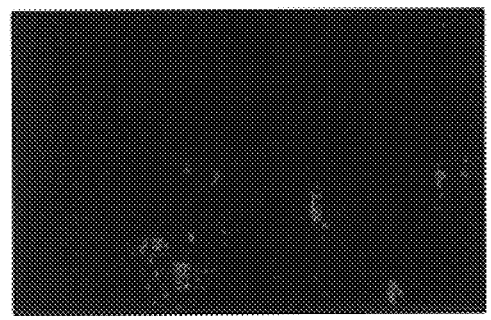
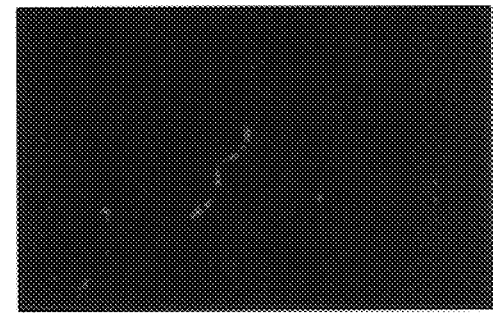
■ 1.0
*FIG. 5C*    *FIG. 5F*

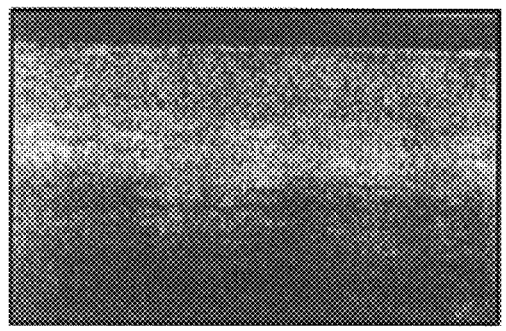
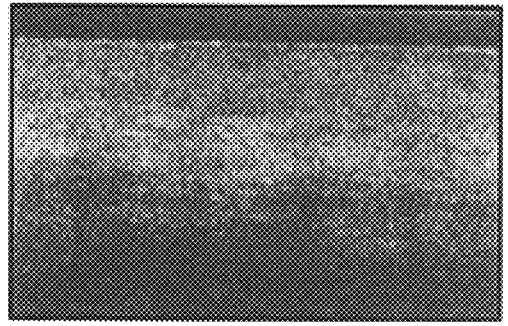
━━━ 250μm  0.0 ━━━━━━ 60dB
FIG. 6A                    FIG. 6D
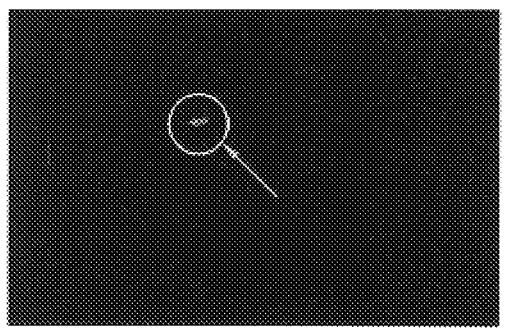
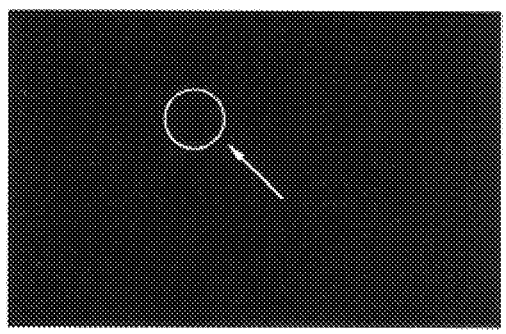
-500 ━━━━━━━ 500 Hz
FIG. 6B                    FIG. 6E
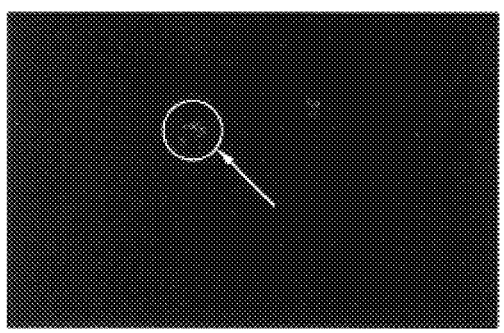
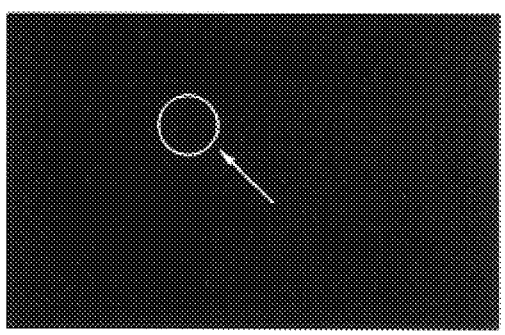
0.0 ━━━━━━ 1.0
FIG. 6C                    FIG. 6F

PHASE-RESOLVED OPTICAL COHERENCE TOMOGRAPHY AND OPTICAL DOPPLER TOMOGRAPHY FOR IMAGING FLUID FLOW IN TISSUE WITH FAST SCANNING SPEED AND HIGH VELOCITY SENSITIVITY

RELATED APPLICATIONS

The present application is further a continuation in part application of copending application Ser. No. 09/096,434 filed Jun. 11, 1998, which is assigned to the same assignee as the present application.

This application is related to U.S. Provisional Patent Application Ser. No. 60/135,363, filed on May 21, 1999.

BACKGROUND OF THE INVENTION

1. Field of the Invention

The field of the invention relates to in vivo scanning of tissue using optical coherence tomography.

2. Description of the Prior Art

Direct visualization of tissue physiology and anatomy provides important information to the physician for the diagnosis and management of disease. High spatial resolution noninvasive techniques for imaging in vivo tissue structure and blood flow dynamics are currently not available as a diagnostic tool in clinical medicine. Such techniques could have a significant impact for biomedical research and patient treatment. Techniques such as Doppler ultrasound (DUS) and laser Doppler flowmetry (LDF) are currently used for blood flow velocity determination. DUS is based on the principle that the frequency of ultrasonic waves backscattered by moving particles are Doppler shifted. However, the relatively long acoustic wavelengths required for deep tissue penetration limits the spatial resolution of DUS to approximately 200 $\mu$m. Although LDF has been used to measure mean blood perfusion in the peripheral microcirculation, high optical scattering in biological tissue limits spatial resolution.

Optical Doppler tomography (ODT), also termed Doppler optical coherence tomography, is a recently developed optical technique for imaging both the tissue structure and the flow velocity of moving particles in highly scattering media. The noninvasive nature and exceptionally high spatial resolution of ODT have many potential applications in the clinical management of patients in whom the imaging of tissue structure and the monitoring of blood-flow dynamics are essential. Examples include burn-depth determination, evaluation of the efficiency of laser treatment of port wine stains, photodynamic therapy monitoring, and brain injury evaluation.

An example of an in vivo ODT imaging system with high spatial resolution and accurate blood-flow velocity measurements in vessels in rodent skin as been described by the present inventors, see Z. Chen, T. E. Milner, D. Dave, and J. S. Nelson, Opt. Left. 22, 64 (1997); and Z. Chen, T. E. Milner, S. Srinivas, X. Wang, A. Malekafzali, M. J. C. van Gemert, and J. S. Nelson, Opt. Lett. 22,1119 (1997).

However, previously developed ODT systems were unable to achieve simultaneously both high imaging speed and high velocity sensitivity, which are essential for measuring blood flow in human skin.

ODT combines the Doppler principle with optical coherence tomography (OCT) to yield high-resolution tomographic images of static and moving constituents simultaneously in highly scattering biological tissues. The flow velocity of moving particles in the sample can be determined by measurement of the Doppler shift of the fringe frequency with a short-time Fourier transform. Since detection of the Doppler shift requires sampling the interference fringe intensity over at least one oscillation cycle, the minimum detectable Doppler frequency shift ($\Delta f_D$) varies inversely with the short-time Fourier transform window size ($\Delta t_p$) at each pixel (i.e., $\Delta f_D \approx 1/\Delta t_p$). For a given time-window size at each pixel, the velocity sensitivity ($v_{min}$) is given by $$v_{min} = \frac{\lambda_0}{2n\cos(\theta)\Delta t_p}$$

where $\lambda_0$ is the light-source center wavelength, n is the sample's refractive index, and $\theta$ is the angle between the probing beam and the direction of flow. Therefore, the higher the value of $\Delta t_p$, the higher the velocity sensitivity. However, spatial resolution, $\Delta x_p$, is proportional to the short-time Fourier transform window size and is given by $$\Delta x_p = V \Delta t_p,$$

where V is the one-dimensional scanning speed of the ODT system. Consequently, velocity sensitivity and spatial resolution are coupled. A large pixel time-window size increases velocity sensitivity while decreasing spatial resolution. Increasing the image frame rate also decreases velocity sensitivity. For example, for a rate of one frame per second for an image with 100×100 pixels, the maximum data-acquisition time for each pixel ($\Delta t_p$) is 1/10,000 s. Accordingly, the minimum resolvable Doppler frequency shift is 10 kHz, which corresponds to a velocity sensitivity of approximately 25 mm/s for $\lambda_0$=1300 nm and $\theta$=80°. To measure blood flow in small vessels in which red blood cells are moving at low velocity, one must reduce the imaging frame rate if the spectrogram method is used. When ODT goes to real-time imaging, the time for each axial scan (A scan) is very short. As a result, the velocity sensitivity decreases dramatically, because the window time for each pixel is so short that a fast Fourier transform algorithm cannot detect any large Doppler frequency shift.

BRIEF SUMMARY OF THE INVENTION

The invention is a fast-scanning ODT system that uses phase information derived from a Hilbert transformation to increase the sensitivity of flow velocity measurements while maintaining high spatial resolution. The significant increases in scanning speed and velocity sensitivity realized by the invention make it possible to image in vivo blood flow in human skin. Signal processing according to the invention can be performed in a computer, a digital signal processor, in a phase lock-in amplifier, in a polarized optical system or any device now known or later devised which is equivalent thereto.

The method of the invention overcomes the inherent limitations of the prior art ODT by using a phase change between sequential line scans for velocity image reconstruction. The ODT signal phase can be determined from the complex function, $\tilde{\Gamma}_{ODT}(t)$, which is determined through analytic continuation of the measured interference fringes function, $\Gamma_{ODT}(t)$, by use of a Hilbert transformations, namely:

$$\tilde{\Gamma}_{ODT}(t) = \Gamma_{ODT}(t) + \frac{i}{\pi} P \int_{-\infty}^{\infty} \frac{\Gamma_{ODT}(\tau)}{\tau - t} d\tau = A(t)\exp[i\varphi(t)]$$

where P denotes the Cauchy principle value and A(t) and $\psi$(t) are the amplitude and the phase of $\tilde{\Gamma}_{ODT}(t)$ respectively.

The phase change in each pixel between sequential A-line scans is then used to calculate the Doppler frequency shift:

$$\omega = \Delta\psi/T$$

where T is the time interval between successive A scans. Because T is much longer than the pixel time window, very small Doppler shifts can be detected with this technique. For example, in an OCT/ODT image with 100×100 pixels, if the data-acquisition time at each pixel is 100 $\mu$s, using the phase difference between sequential A-line scans increases the time window from 100 $\mu$s to 100×100 $\mu$s=10 ms. Therefore, the frequency resolution improves from 10 kHz to 100 Hz, and the velocity sensitivity improves from 3 mm/s to 30 $\mu$m/s. In addition, spatial resolution and velocity sensitivity are decoupled. Furthermore, because two sequential A-line scans are compared at the same location, speckle modulations in the fringe signal cancel each other and, therefore, will not affect the phase-difference calculation. Consequently, the phase-resolved method reduces speckle noise in the velocity image. Finally, if the phase difference between sequential frames is used, then the velocity sensitivity can be increased further.

The invention now having been briefly summarized, turn to the following drawings wherein the invention and its operation may be more easily visualized.

BRIEF DESCRIPTION OF THE DRAWINGS

FIG. 1 is a schematic diagram of the optical device and signal processing system using the method of the invention for ODT imaging. The system comprises a rapid scanning optical delay line (RSOD); a fiber-pigtailed electro-optic modulator (EOM); a superluminescent diode (SLD); and an analog-digital converter (A/D). The RSOD is conventional and is further described in G. J. Tearney et. al., "*High-Speed Phase- and Group-Delay Scanning with a Grating-Based Phase Control Delay Line,*" Optics Letters, vol. 22, No. 23, pp 1811–1813 (1997). A probe is mounted upon a stage for lateral scanning.

FIG. 2A is a gray-scale structural image. FIG. 2B is a grey scale-coded velocity image of blood flow. FIG. 2C is a graph of Doppler frequency shifts (velocity profile) along a vertical cross section passing through the largest vein in the velocity image indicated by arrow 1 in FIG. 2B. FIG. 2D is a graph of the Doppler frequency shifts of a 20 $\mu$m capillary indicated by arrow 2 in FIG. 2B.

FIGS. 3A and B are photographs of OCT/ODT images of blood flow in human skin (hand palm). FIG. 2A is a gray-scale structural image. FIG. 2B is a grey scale coded velocity image of blood flow.

FIGS. 5A–5F are photographs of the cross-sectional structural and velocity images of a port wine stain, PWS, located on the left upper extremity of a human.

FIGS. 6A–6F are photographs which show the results in response to a 12 J/cm$^2$ therapeutic laser pulse. FIGS. 6A and 6D show structural images. FIGS. 6B and 6E are velocity images. FIGS. 6C and 6F are variance images.

Figures 2A, 2B:
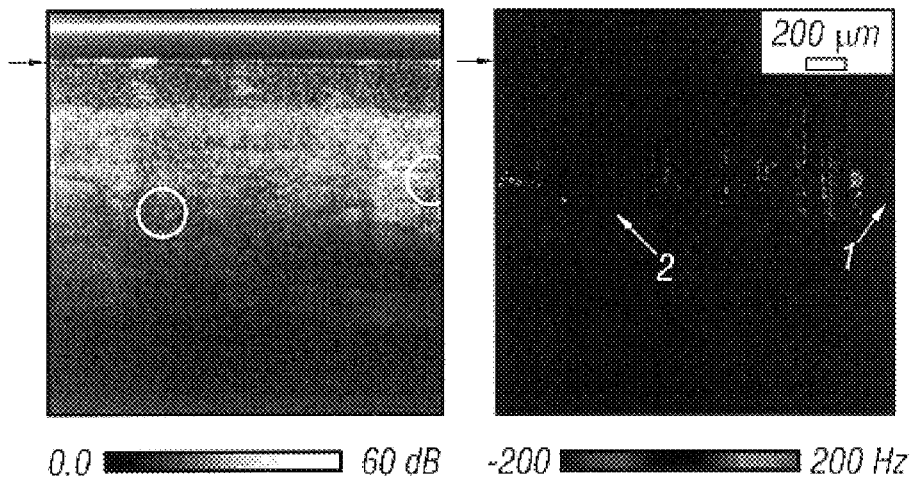
FIGS. 2A and 2B are photographs which show ODT blood-flow images.

The invention and its various embodiments may now be visualized by turning to the following detailed description of the preferred embodiments. What is described is an illustrated embodiment, which should be taken as limiting the invention which is more described and defined in the following claims.

DETAILED DESCRIPTION OF THE PREFERRED EMBODIMENTS

Numerous methodologies have been investigated in search of the ideal blood flow imaging technique for human skin, including: fluorescein injection, isotopic clearance, angioscopy and angiography, electromagnetic flowmetry, interstitial fluid pressure, transcutaneous $pO_2$, reflective photoplethysmography, dermofluorometry, magnetic resonance imaging, and temperature probes. Inasmuch as all of these methods shown but limited utility, more recent approaches have incorporated the Doppler effect.

Optical Doppler Tomography (ODT) combines Doppler velocimetry with optical coherence tomography (OCT) to measure blood flow velocity at discrete user-specified locations in highly scattering biological tissues. The exceptionally high resolution of ODT allows noninvasive imaging of both in vivo blood microcirculation and tissue structures surrounding the vessels. What is described below is a novel phase resolved OCT/ODT system that uses phase information derived from a Hilbert transformation to image blood flow in human skin with fast-scanning speed and high velocity sensitivity. The phase resolved system of the invention decouples spatial resolution and velocity sensitivity in flow images and increases imaging speed by more than two orders of magnitude without compromising spatial resolution and velocity sensitivity. The minimum blood flow velocity that can be detected in human skin is as low as 10 $\mu$m/s while maintaining a spatial resolution of 10 $\mu$m. The noninvasive nature and high spatial resolution of ODT should be very useful in the clinical management of patients in whom imaging blood flow in human skin is required.

However, flow velocity imaging is limited by the fact that the Doppler frequency shift depends on the angle between the probe and flow directions and is very sensitive to the pulsatile nature of the blood flow. In many clinical applications, the location of the microvasculature is more important than the absolute value of the flow velocity. Here the phase resolved OCT/ODT technique is extended and what is described is a method that uses variance of the Doppler frequency spectrum to map the microvasculature. This method has the advantage that it is less sensitive to the pulsatile nature of blood flow and provides better mapping of vessel location. In addition, this method can also be used to study turbulence and separate Doppler shift due to biological flow from the background motion of the tissue under study.

The invention is a fast-scanning ODT system that uses phase information derived from a Hilbert transformation to increase the sensitivity of flow velocity measurements while maintaining high spatial resolution. The illustrated embodiment is directed to applications to biological tissue without restriction, however, the invention must be understood to be applicable to any type of sample having a material flow or movement therein, including nonbiological samples or objects. Similarly, while the invention is illustrated by using laser generated light, at least partially coherent radiation or energy of any frequency can be employed and is included within the scope of the invention.

The significant increases in scanning speed and velocity sensitivity realized by the invention make it possible to image in vivo blood flow in human skin. The method of the invention overcomes the inherent limitations of the prior art ODT by using a phase change between sequential line scans for velocity image reconstruction. The ODT signal phase or phase shifts at each pixel can be determined from the complex function, $\Gamma_{ODT}(t)$, which is determined through analytic continuation of the measured interference fringes function, $\Gamma_{ODT}(t)$, by use of a Hilbert transformation, by electronic phase demodulation, by optical means, or a fast Fourier transformation. The phase change in each pixel between axial-line scans is then used to calculate the Doppler frequency shift. Sequential measurements of a single line scan, measurements of sequential line scans or measurements of line scans in sequential frames may be used. Because the time between line scans is much longer than the pixel time window, very small Doppler shifts can be detected with this technique. In addition, spatial resolution and velocity sensitivity are decoupled. Furthermore, because two axial-line scans are compared at the same location, speckle modulations in the fringe signal cancel each other and, therefore, will not affect the phase-difference calculation.

What is first described is the methodology of the invention in an illustrated embodiment in the context of FIGS. 4–6F. Then the apparatus of the invention will be described in the context of FIGS. 1–3B. The methodology of the invention is described using the illustration of a port wine stain in skin. Port wine stain (PWS) is a congenital, progressive vascular malformation of capillaries in the dermis of human skin that occurs in approximately 0.7% of children. Histopathological studies of PWS show an abnormal plexus of layers of dilated blood vessels located 150–750 μm below the skin surface in the upper dermis, having diameters varying on an individual patient basis, and even from site to site on the same patient, over a range of 10–150 μm. The pulsed dye laser can coagulate PWS selectively by inducing microthrombus formation within the targeted blood vessels. In these preliminary studies conducted on PWS patients, the feasibility and potential application of phase resolved OCT/ODT to characterize and image blood flow with high spatial resolution is proven.

The optical device is based on a phase resolved OCT/ODT system according to the invention and the detailed experimental set up is described below in connection with FIG. 1. Briefly, low-coherence light generated by amplified spontaneous emission (ASE) of a 1300 nm diode is coupled into the source arm of a fiber-based Michelson interferometer 12. In the reference arm 15, a rapid-scanning optical delay line 14 (RSOD) is used for axis scanning. The RSOD employs a grating 16 to control the phase- and group-delays separately and is aligned such that no phase modulation is generated when the group-delay is scanned. A fiber-based electro-optic phase modulator 18 (EOM) is inserted in the reference arm 15 to produce a stable carrier frequency. The RSOD 14 (for A-scan) is run at 1000 Hz and the voice-coil stage 21 (for L-scan) is driven linearly at a speed of 500 μm/s. The signal is digitized with a 12 bit 5 MHz A/D converter 22. In conventional OCT, the fringe signal from each A-line scan is used to calculate the Doppler shift of the power spectrum using a short-time Fourier transformation (STFT) algorithm. Because the time window used in STFT is inversely proportional to the A-line scanning speed, the velocity sensitivity is limited by A-line scanning speed. In the phase resolved OCT/ODT of the invention, phase change of interference fringe between sequential A-line scans is used to calculate the Doppler frequency shift. Consequently, the phase resolved system of the invention decouples spatial resolution and velocity sensitivity in flow images and increases imaging speed by more than two orders of magnitude without compromising spatial resolution and velocity sensitivity.

Figure 4:
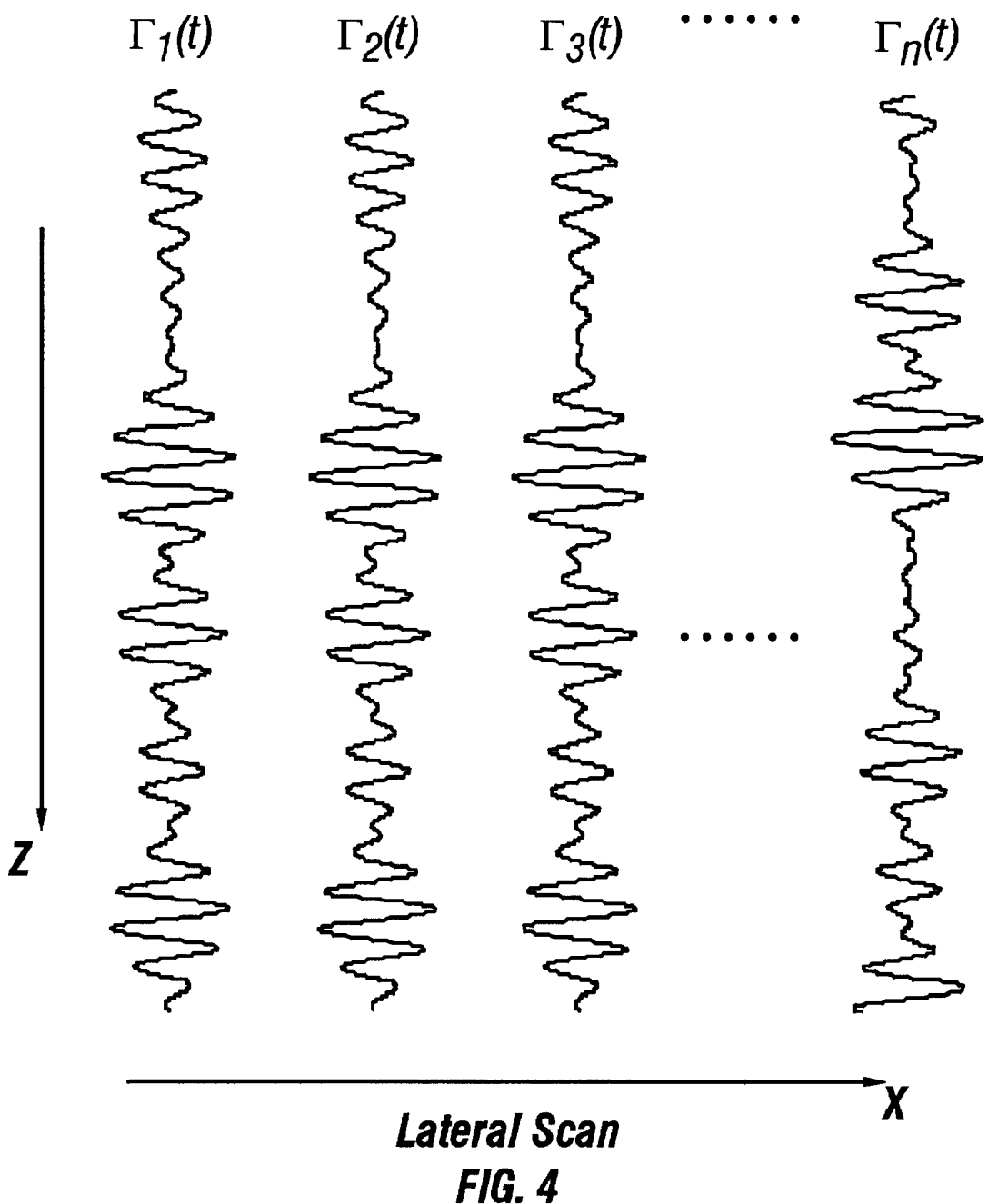
FIG. 4 is a graph illustrating the data input of the measured interference fringes function, $\Gamma_{ODT}(t)$, in an areal scan.

The digitized fringe signal, $\Gamma_j(t)$, is first passed through a digital bandpass filter in module 38 in FIG. 1 to increase the signal to noise ratio (SNR). The traces shown in FIG. 4 are then obtained for a scan area. The complex function $\tilde{\Gamma}_j(t)$ is then determined through an analytic continuation using the Hilbert transformation in module 38:

$$\tilde{\Gamma}_j(t) = \Gamma_j(t) + \frac{i}{\pi} P \int_{-\infty}^{\infty} \frac{\Gamma_j(\tau)}{\tau - t} d\tau \tag{1}$$

where j denote jth A-line scan and P denotes the Cauchy principle value. The Doppler frequency shift is determined from the average phase shift between sequential A-scans in module 40 using the following equation:

$$\Delta f = \frac{1}{2\pi T} \tan^{-1} \left( \frac{\mathrm{Im}\left(\sum_{j=1}^{n} \tilde{\Gamma}_j \cdot \tilde{\Gamma}_{j+1}^*\right)}{\mathrm{Re}\left(\sum_{j=1}^{n} \tilde{\Gamma}_j \cdot \tilde{\Gamma}_{j+1}^*\right)} \right) \tag{2}$$

where T is the time interval between sequential scans, and n is the number of sequential scans averaged. To increase the SNR in ODT images, not less than three and preferably at least eight sequential A-line scans are averaged. Other choices could be used if desired. The standard deviation of the Doppler frequency spectrum, σ, is calculated by the following:

$$\sigma^2 = \frac{\int_{-\infty}^{\infty} (\omega - \bar{\omega})^2 P(\omega) d\omega}{\int_{-\infty}^{\infty} P(\omega) d\omega} = \frac{1}{T^2} \left( 1 - \frac{\left|\sum_{j=1}^{n} \tilde{\Gamma}_j \cdot \tilde{\Gamma}_{j+1}^*\right|}{\sum_{j=1}^{n} \tilde{\Gamma}_j \cdot \tilde{\Gamma}_j^*} \right) \tag{3}$$

where P(ω) is the Doppler power spectrum and $\bar{\omega}$ is the centroid value of the Doppler frequency shift. The value for σ depends on the flow velocity distribution. Variations in flow velocity will broaden the Doppler frequency spectrum and result in a larger σ value.

Cross-sectional structural and velocity images of a PWS located on the left upper extremity of a human volunteer, obtained by the system are shown in FIGS. 5A–5F. The scanning range is 2 mm (lateral) by 2 mm (axial) but only the linear part (1.25 mm) of the axial scan is shown in FIGS. 5A–5F. The image size is 800 (lateral) by 500 (axial) pixels with a size of 2.5 μm/pixel, which keeps the image resolution consistent with the coherence length of the light source (10 μm). To prevent surface movement, the area imaged was in contact with a glass window and an index-matching oil was inserted between the glass and PWS to decrease light reflection from the skin surface. The index-matching oil also helped to flatten the skin surface so that the wavefront distortion of the probing beam at the skin surface is minimized. FIG. 5A (structural image), FIG. 5B (velocity image) and FIG. 5C (variance image) are taken from the palmer surface of the ring finger. FIGS. 5D, 5E and 5F are taken from the forearm. In addition to an organized network of collagen fibers in the dermis, the epidermal-dermal boundary is clearly noted in the structural images in FIGS. 5A and 5D. Many PWS vessels are detected in the dermis between 400 μm and 1 mm below the skin surface in the velocity images in FIGS. 5B and 5E.

In addition, flow turbulence, which is determined be the standard deviation, σ, of the Doppler spectrum due to the variance of the velocity distribution, is shown as two dimensional images in FIGS. 5C and 5F. As can be seen, it is much easier to identify the PWS blood vessels in the a images in FIGS. 5C and 5F as opposed to the velocity images in FIGS. 5B and 5E. This can be attributed to the pulsatile nature of blood flow. Given the fact that blood flow turbulence is only determined by the physical characteristics of blood and vessel structure, determining the variance provides a much more accurate mapping of the subsurface microvasculaure in human skin.

In order to monitor the efficacy of PWS laser treatment in situ, a hand piece was constructed that combines the therapeutic beam with the OCT/ODT beam. The OCT/ODT image can be taken right after the therapeutic laser pulse without replacing of the probing beam. The laser used for PWS treatment is a ScleroPlus® pulsed dye laser (Candela Laser Corp, Wayland, Mass.) with a wavelength of 595 nm and pulse-width of 1.5 ms. FIGS. 6A–6F show the results in response to a 12 J/cm² therapeutic laser pulse. In the structural images in FIGS. 6A and 6D, there is no visible difference before and after laser exposure, which implies that the adjacent skin structures were not affected by the treatment. In the velocity images in FIGS. 6B and 6E and variance images in FIGS. 6C and 6F, however, no blood flow is noted after laser exposure indicative of irreversible microthrombus formation in the PWS blood vessels. Blood flow did not return to pre-treatment values as determined by subsequent scans made up to 24 hours after laser exposure.

The rationale for using ODT in the clinical management of PWS is that the technique offers a means of providing a fast semi-quantitative evaluation of the efficacy of laser therapy in real-time. If partial restoration of flow occurs immediately or shortly after pulsed laser exposure, indicative of reperfusion due to inadequate blood vessel injury, the PWS can be retreated using higher light dosages. Retreatment is continued until the measured Doppler shift is zero due to a permanent reduction in blood flow, indicative of irreversible microthrombus formation in the PWS vessels.

In summary, what has been developed is a new imaging method, which uses velocity variance to determine the location and shape of blood vessels below the skin surface. It has been shown here that phase resolved OCT/ODT can be used to image blood flow in PWS human skin by providing a fast semi-quantitative evaluation of the efficacy of PWS laser therapy in situ and in real-time on an individual patient basis.

Figure 7:
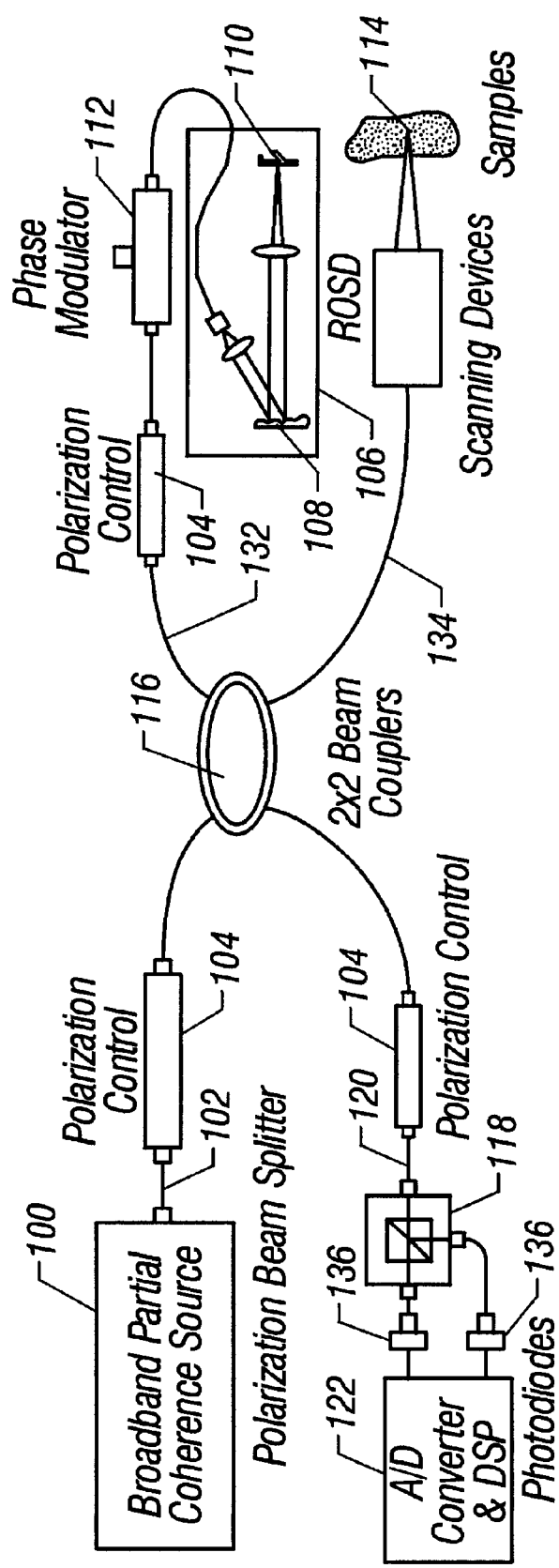
FIG. 7 is a diagram of an interferometer of another embodiment of the invention.

The operation of the system of the invention now having been described in the illustration of port wine stain treatment in skin, turn now to consider the structure of the apparatus used for implementing the method. A schematic of the optical device and signal processing algorithm is shown in FIG. 7.

Optical coherence tomography (OCT) is a new imaging modality based on coherence domain optical technology. OCT takes advantage of the short coherence length of broadband light sources to perform micrometer-scale, cross-sectional imaging of tissue structure in biological tissue. ODT combines LDF with OCT to obtain high resolution tomographic images of static and moving constituents in highly scattering biological tissues. Localized flow velocity detection with high spatial resolution can be achieved using coherence grating. Using a Michelson interferometer with a low coherence light source, ODT measures the amplitude and frequency of the interference fringe intensity generated between reference and target arms to form structural and velocity images. High spatial resolution is possible because light backscattered from the sample recombines with that from the reference beam and forms interference fringes only when the optical path length difference is within the source coherence length. When light backscattered from a moving constituent interferes with the reference beam, a Doppler frequency shift occurs ($\Delta f_D$) in the interference fringe:

$$\Delta f_D = \frac{1}{2\pi}(\vec{k}_s - \vec{k}_i) \cdot \vec{v}$$

where $k_i$ and $k_s$ are wave vectors of incoming and scattered light, respectively, and v is the vector velocity of the moving particle. With knowledge of the angle between ($k_s - k_i$) and v, measurement of the Doppler frequency shift ($\Delta f_D$) allows determination of particle velocity at discrete user-specified locations in turbid samples.

The first prototype system which was built by the inventors had an acquisition time is on the order of minutes, which is too long to be practical for clinical applications. The embodiment of FIG. 1 is not subject to such limitations. There are two factors that limit the speed in the prototype OCT/ODT system. First, the scanning of the delay line in the prototype ODT system use mechanical linear translation which limits the speed to 100 mm/sec. Second, ODT images are constructed using spectrogram calculated from the power spectrum with a short time Fourier transformation (STFT). There are two limitations to velocity calculation using a spectrogram. The first limitation is that the noise from the power spectrum is always positive, which creates a problem when using the centroid method to determine the Doppler frequency shift. The limited bandwidth tends to underestimate the velocity when the signal to noise ratio is small. The second limitation comes from the conflict between spatial and velocity resolution. When STFT is used to calculate flow velocity, the accuracy is determined by the window size of the Fourier transformation for each pixel. Although a large time window increases velocity resolution, spatial resolution decreases. For high spatial resolution OCT/ODT, the window size must be limited to within the source coherence length. In addition, as the spatial resolution increases, the number of fringes within the source coherence decreases. For example, within the coherence length of 5 μm, the number of interference fringes is less than 7. When STFT is used to calculate the power spectrum, the accuracy of velocity determination decreases significantly when the fringe number is reduced.

In the embodiment of FIG. 7, a phase resolved OCT/ODT system is describes which overcomes these limitations. The design uses both amplitude and phase of the interference fringe for structure and flow velocity image reconstruction.

A schematic diagram of the phase resolved OCT/ODT system in shown in FIG. 7. A broadband partial coherence source 100 is coupled into a single mode fiber 102. Polarization control devices 104 are inserted into fiber 102 and elsewhere in the fiber interferometer of FIG. 7 to control the polarization states of the light. A rapid-scanning optical delay (ROSD) line 106 is used for group phase delay or depth scanning. ROSD is based on the principle that a linear phase ramp in the frequency domain produces a delay in the time domain. A grating 108 in the delay line is used to spread the spectrum of the source across a galvanometer-mounted mirror 110. Tilting mirror 110 introduces an optical path delay that varies linearly with the wavelength. The resulting group-delay $I_g$ is given by:

$$I_g(\gamma) = \frac{4f\lambda_0\gamma}{d\cos(\theta_0)}$$

where $\gamma$ is the mirror angle, f is the focal length of the lens, d is the grating spacing, $\theta_0$ is the diffracted angle of the center wavelength, and $\lambda_0$ is the center wavelength of the source. Because ROSD 106 can uncouple the group delay from the phase delay, an electro-optical phase modulator 112 is introduced to produce a stable high carrier frequency. This is important because the accuracy of the ODT velocity measurement depends on the carrier frequency stability. Compared to previous ODT designs where mechanical or piezo scanning is used, electro-optical phase modulation produces a more stable carrier frequency.

Light reflected from sample 114, which is the biological target, is recombined with that from the reference beam in the 2×2 beam from RSOD 106 in coupler 116 to form interference fringes. A polarization beam splitter 118 is used in the detection arm 120 to split the signal into two perpendicular polarization states. The signal is then digitized with an A/D converter 122. The detected signals from two polarization channels are combined to form a polarization independent interference signal. This has the advantage of removing artifacts due to fiber bending or birefringence in the biological sample. In addition, noise due to the speckle pattern is reduced.

Figure 8:
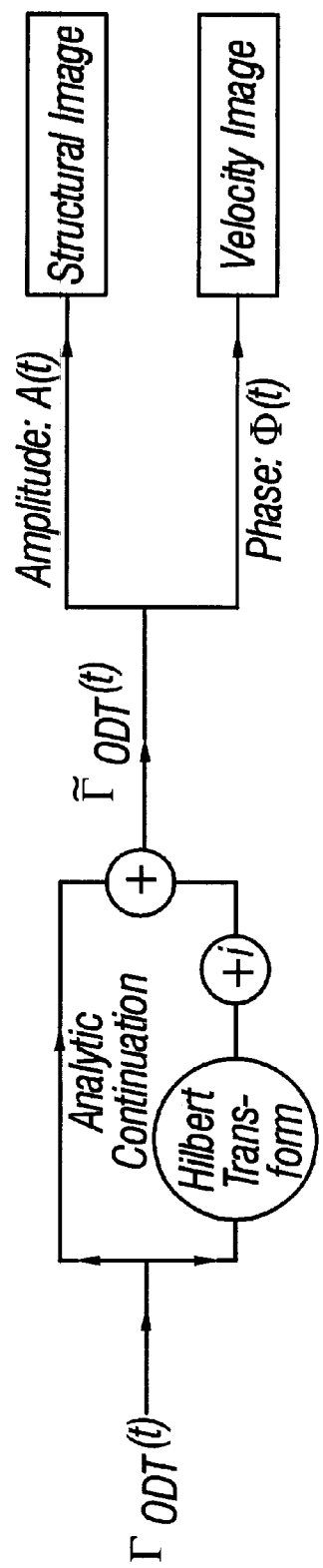
FIG. 8 is a diagram of a first embodiment illustrating the methodology of the invention.

In a conventional OCT, only the amplitude of the interference fringe is used to calculate the Doppler shift from the power spectrum. The design of the invention calculates both amplitude and phase using a digital signal processing (DSP) module 122 in real time. The schematic diagram for the image reconstruction algorithm performed in module 122 is shown in FIG. 8.

The complex valued interference fringe function, $\Gamma_{ODT}(t)$, is determined through analytic continuation of the measured interference fringes, and can be accomplished by two different methods as described below. The amplitude A(t) and phase $\psi(t)$ of $\Gamma_{ODT}(t)$ can then be calculated. The amplitude is then used to reconstruct the structural image. If there is flow in the sample being imaged, the phase change provides flow velocity information because of the Doppler frequency shift. The derivative of the phase is then used to reconstruct the velocity image. Because the amplitude and phase information can be determined simultaneously for each sampling point of the A/D converter, one can calculate the velocity at each sampling point and the accuracy of the Doppler frequency shift will not be limited by the window size.

Figure 9:
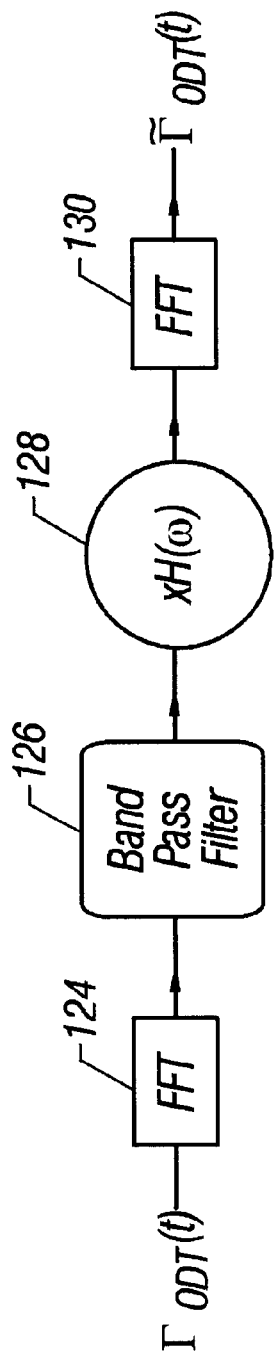
FIG. 9 is a diagram of a second embodiment illustrating the methodology of the invention.

There are two methods for determining $\Gamma_{ODT}(t)$. The first method uses fast Fourier transformation (FFT) with the DSP module 122 as diagrammatically depicted in FIG. 9. In this method, the time domain fringe signal is first Fourier transformed at step 124, and then passed though a band pass filter at step 126 to reduce noise. The signal is then multiplied by the Heaviside function H($\omega$) at step 128. $\Gamma_{ODT}(t)$ can then be obtained with a second FFT at step 130. All algorithms can be performed in real time with DSP module 122.

Figure 10:
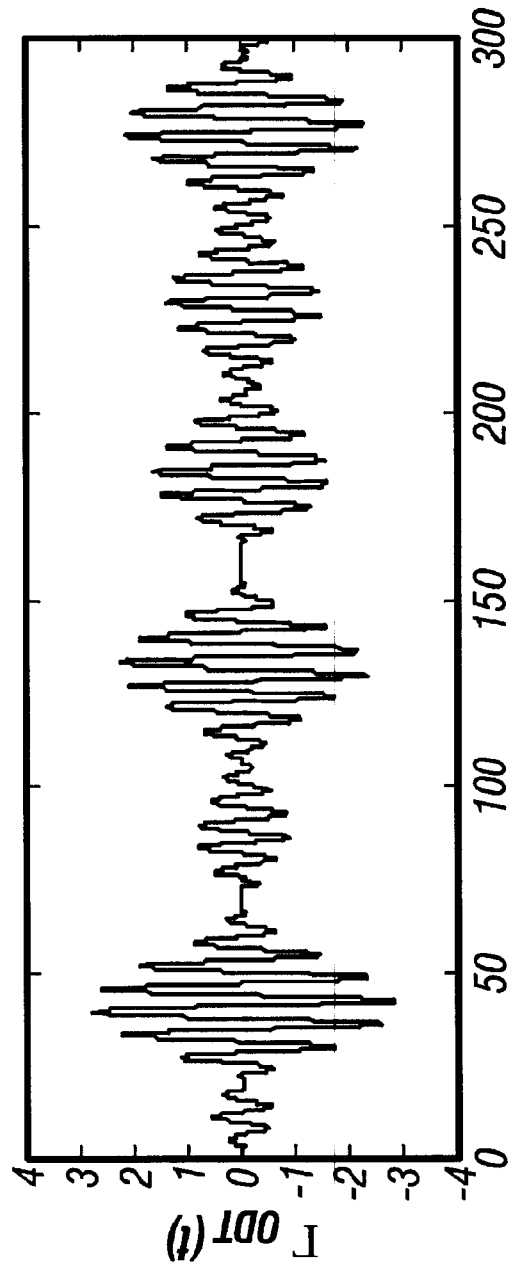
FIG. 10 is a graph showing a typical interference fringe as a function of time.
Figure 11A:
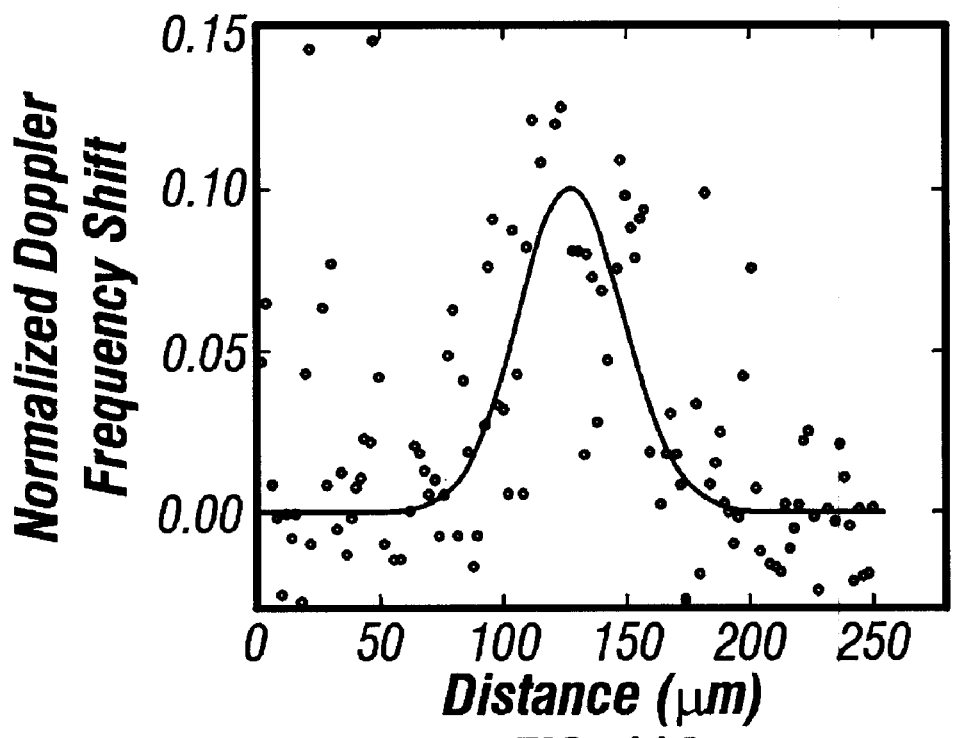
FIGS. 11A and 11B a velocity profiles reconstructed from simulation data using a power spectrum method and a phase resolved Hilbert transformation of the invention respectively.
Figure 11B:
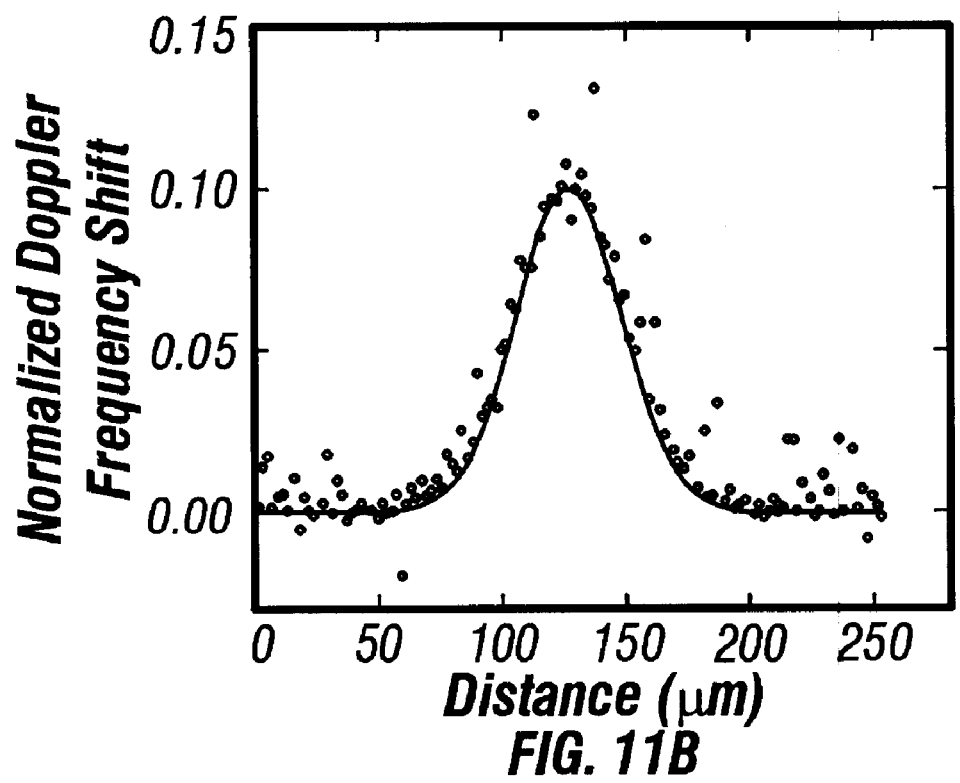

Computer simulations have been performed to compare the phase resolved method with the power spectrum method. The interference fringe signal generated from flow with a Gaussian velocity profile (center at $t_0$, width b) was simulated as:

$\Gamma_{ODT}(t) = A(t) \cos(\psi(t))$ where A(t) is given by:

$$\frac{d\varphi}{dt} = \omega\left(1 + ce^{\frac{-(t-t_0)}{b}}\right)$$

where c denotes the ratio of the Doppler frequency shift to the carrier frequency at the peak of the velocity profile. A(t) is the amplitude modulation due to the tissue inhomogeneity. A typical interference fringe signal is shown in FIG. 10. Random discontinuity at zero crossing was included in the fringe signal to simulate optical statistical properties of particles in the flow and tissue, such as speckle induced signal fluctuations. Using the power spectrum method for flow velocity determination, the simulation result is shown in FIG. 11A. For comparison, the velocity profile reconstructed using phase resolved method under the same condition is shown in FIG. 11B. The simulation results indicate that the phase resolved method gives much higher accuracy in reconstructing the velocity profile as compared to that using the power spectrum. When the Doppler frequency shift is as low as 1% of the carrier frequency, the phase resolved method can easily reconstruct the velocity profile. The minimum velocity that can be resolved by phase determination is a factor of 10 smaller than that using the power spectrum.

Figure 12A:
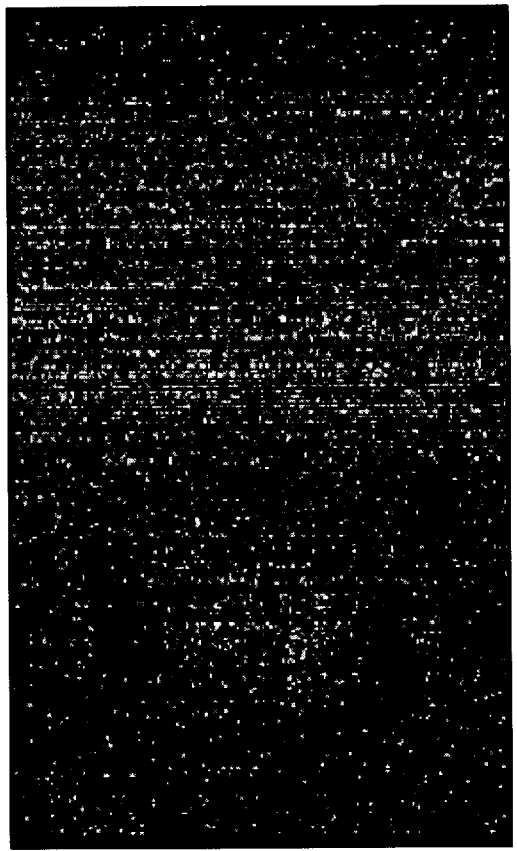
FIGS. 12A and 12B a velocity profiles of a phantom using a power spectrum method and a phase resolved Hilbert transformation of the invention respectively.
Figure 12B:
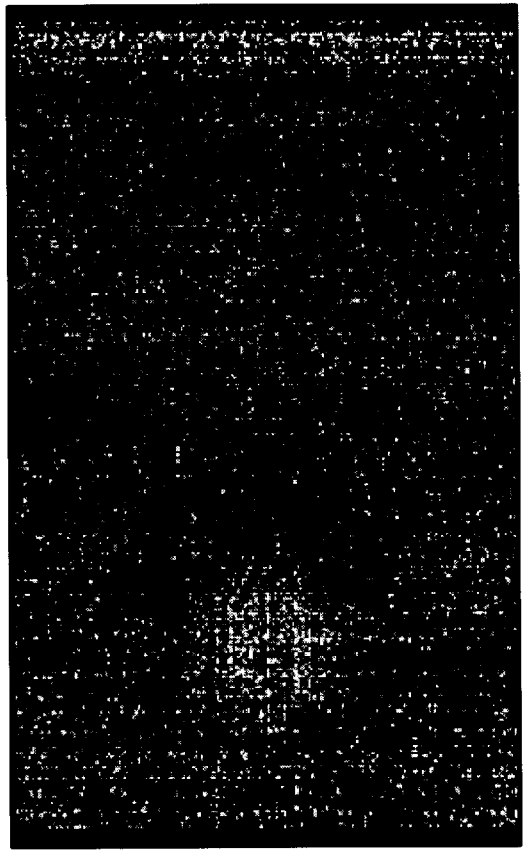

To confirm our simulation results, in vitro flow measurements were performed on a phantom system comprising a plastic tube with a lumen diameter of 300 $\mu$m submerged in 0.1% intralipid gel. An intralipid solution at a concentration of 0.2% was injected into the tube with an average flow velocity of 50 $\mu$m/s. The angle between the probing beam and flow direction was 75°. The carrier frequency of the fringe signal was 8.3 kHz and the Doppler frequency shift induced due to the flow was less than 1% of the carrier frequency. FIG. 12A shows the velocity image using the power spectrum method. For comparison, the image shown on FIG. 12B was reconstructed using phase resolved method. The experimental results clearly indicate that the phase resolved method can measure the velocity flow profile much more accurately than that of the power spectrum method.

Figure 13:
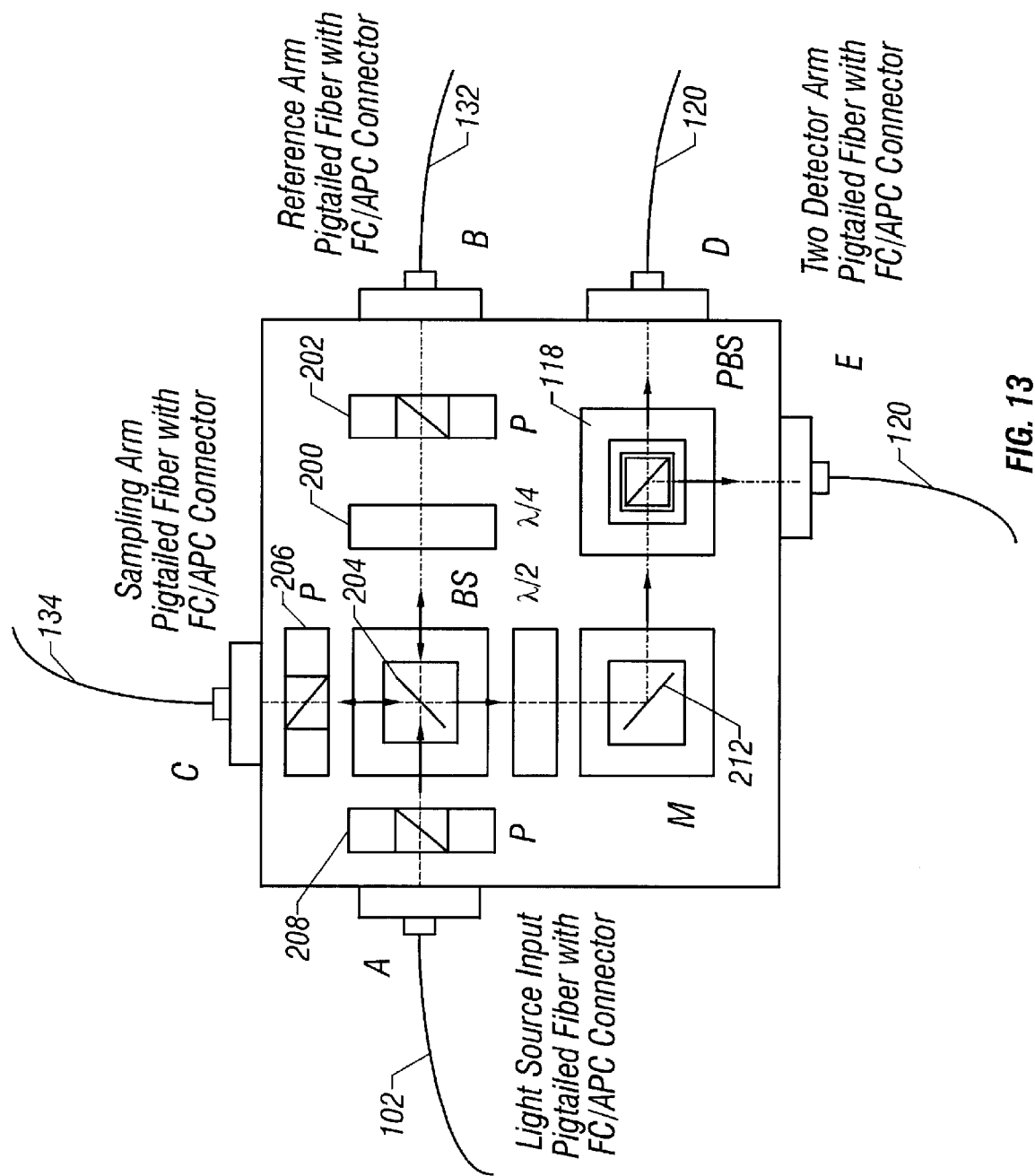
FIG. 13 is a diagram illustrating another embodiment of the invention wherein the real and imaginary parts of the interference data fringes are separately generated by optical means.

There is another method to compute $\Gamma_{ODT}(t)$ depicted in FIG. 13. This method uses optical polarization to generate two quadrant signals: one corresponds to the real part of the complex signal and the other corresponds to the imaginary part. The advantage of this method is that no FFT transformation is needed to obtain $\Gamma_{ODT}(t)$ and real-time image display can be implemented. The optical setup of this method as shown in FIG. 13 is identical to FIG. 7 except for the following modifications. Linearly polarized light is provided from polarization control 104 in source arm 102 by means of linear polarizer 208. Polarization control 104 coupled to reference arm 132 is adjusted such that the beam coupling back to 2×2 coupler 116 or, in the embodiment of FIG. 13, beam splitter 204 is circularly polarized. This is realized by a quarter wave plate 200 disposed between beam splitter 204 and linear polarizer 202. Light to and from reference arm 132 thus passes twice through quarter wave plate 200 and linear polarizer 202. Polarization control 104 coupled to sampling arm 134 is adjusted such that the beam coupling back to 2×2 coupler 116 or beam splitter 204, is linearly polarized by linear polarizer 206. Polarization control 104 coupled to detection arm 120 is adjusted such that a polarizing beam splitter 118 inserted before the detectors 136 is at 45° with respect to the polarization plane of the beam backscattered from sample 114. This is realized by directing mixed light from beam splitter 204 to half wave plate 210 to mirror 212 and thence to polarizing beam splitter 118. The AC photocurrent of the two detectors 136 coupled to polarizing beam splitter 118 measures the interference between circularly and a linearly polarized light and is given by:

$$\Gamma_1(t)=A(t)\cos(\psi(t))$$
$$\Gamma_2(t)=A(t)\sin(\psi(t))$$

Where $\Gamma_1(t)$ and $\Gamma_2(t)$ are the AC photon currents measured from the horizontal and vertical channels, respectively. Because $\Gamma_1(t)$ and $\Gamma_2(t)$ are exactly 90° phase shifted, on can construct $\Gamma_{ODT}(t)$ as:

$$\Gamma_{ODT}(t)=\Gamma_1(t)+i\Gamma_2(t)$$

This method does not require a high speed DSP. The only computation needed to reconstruct the structure and flow velocity images is to calculate amplitude and phase velocities from $\Gamma_{ODT}(t)$.

Finally, one can also use a phase lock-in amplifier for coherent electronic demodulation of the fringe signal according to conventional design principles. The phase lock-in amplifier would replace the position of the electronics or digital processors in the embodiments of FIG. 1, otherwise all other elements would be substantially identical. The in-phase and quadratic signal components can be used to construct the phase and amplitude information. To get an image of 1 mm×1 mm in less than one second, the reference arm would need to scan as fast as 1 m/s thereby producing an interference fringe frequency of 2 MHz. Few commercially available lock-in amplifiers work well at that high a frequency even when combined with a galvanometric scanner. Furthermore, when the coherence length is less than 5 μm, the integration time of the lock-in amplifier, which determines the signal-to-noise ratio, must be about 5 times the fringe frequency. Thus the shorter integration time required results in a reduced signal-to-noise ratio.

Phase information obtained in the design of the invention can also be used for coherent deconvolution of the OCT image to enhance spatial resolution. Thus, the design enhances resolution in both structure and flow velocity images.

The noninvasive nature and exceptionally high spatial resolution of high speed phased resolved OCT/ODT have distinct applications in the clinical management of patients in whom blood flow monitoring is essential, for example:

Provide an in situ three-dimensional tomographic image and velocity profiles of blood perfusion in human skin at discrete spatial locations in either the superficial or deep dermis;

Burn depth determination; provide guidance regarding the optimal depth for burn debridement prior to definitive closure;

Determination of tissue perfusion and viability immediately after injury, wound closure, replantation, or transposition of either rotational or free skin flaps;

Potential to evaluate the vascular status of a buried muscle flap covered by a split thickness skin graft; perfusion in the superficial and deeper flap components can be monitored separately;

Distinguish between arterial or venous occlusion and determine the presence and/or extent of adjacent post-traumatic arterial or venous vascular injury by providing in situ tomographic image and velocity profile of blood flow;

Monitor the effects of pharmacological intervention on skin microcirculation (e.g., effects of vasoactive compounds or inflammatory mediators; determination of transcutaneous drug penetration kinetics; evaluation of the potency of penetration enhancers; irritation of chemical compounds, patch-test allergens and ultraviolet radiation; comparison of the reactivity of the skin microcirculation in different age and ethnic groups); and Determine the extent of intestinal vascular insufficiency or infarction; to conserve intestine by confining resection to nonvascularized segments.

Measure ocular, e.g. retinal, blood flow.

In addition, phase resolved OCT/ODT can obtain structural and flow images simultaneously with high spatial resolution. Thus, this technology can also be used for clinical diagnosis of tumors (skin, gastrointestinal and respiratory track, larynx, bladder, uterine cervix, etc.)

Finally, phase resolved OCT/ODT is also attractive for the following industrial applications:

Characterization and monitoring of flow velocity when the fluid is encapsulated in highly scattering materials such as fibrous substances or resin composites;

Particle concentration and size, and fluid flow velocity profile may be accurately measured and provide useful diagnostic information for process monitoring and quality control;

Situations involving turbid fluid flow samples such as materials processing of paints, pigmented fluids, and other types of opaque liquids; and Characterization and monitoring of dry particulate flow within conduits such as a jet stream; here, a significant advantage of ODT is that the flow could be characterized and monitored without disturbing the stream.

In summary, we have designed a novel method to image tissue structure and flow velocity with high resolution and high speed. The method uses both amplitude and phase information to reconstruct structural and flow velocity image.

The prior art OCT/ODT systems have a limited velocity sensitivity and image frame rate. This limitation is due to the fact that flow velocity images are reconstructed using a spectrogram calculated from the power spectrum with short time Fourier transformation (STFT). When STFT is used to calculate flow velocity, the accuracy is determined by the window size of the Fourier transformation for each pixel. Inasmuch as detection of the Doppler shift using STFT requires sampling the interference fringe intensity over at least one oscillation cycle, the minimum detectable Doppler frequency shift, $\Delta f_D$, varies inversely with the STFT window size (i.e., $\Delta f_D \approx 1/\Delta t_p$). With a given STFT window size, velocity resolution ($v_{ODT}(\min)$) is given by:

$$V_{ODT}(\min)=\lambda_0/(2n\cos(\theta)/\Delta t_p$$

Therefore, the larger the STFT window size, the better the velocity resolution. However, spatial resolution, $\Delta x_p$, is proportional to the STFT window size and given by:

$$\Delta x_p = v \Delta t_p$$

where v is the one-dimensional scanning speed of the OCT/ODT system. Therefore, velocity resolution and spatial resolution are coupled. A large STFT window size increases velocity resolution while decreasing spatial resolution.

Furthermore, increasing the image frame rate also decreases velocity sensitivity. For example, to achieve one frame per second for an image with 100×100 pixels, the maximum data acquisition time for each pixel ($\Delta t_p$) is 1/1000 second. The minimum resolvable Doppler frequency shift is therefore 10 kHz, which corresponds to a velocity resolution approximately of 3 mm/s. Therefore, if one wants to image red blood cells moving at a low flow velocity, one has to reduce the image frame rate with the spectrogram method. When ODT goes to real-time imaging, the time for each axial scanning (A-Scan) is very small. As a result, the sensitivity to detect the flow velocity decreases dramatically because the window time for each pixel is so small that no significant Doppler frequency shift can be detected by a fast Fourier transform (FE7I) algorithm.

To overcome this limitation, a method is employed that uses the phase change between subsequent line scans for velocity image reconstruction. The phase of the ODT signal can be determined by a Hilbert transformation. (described in the previous section), polarization demodulation described in the previous section, quadratic demodulation, or other demodulation methods. The phase resolved OCT/ODT method is based on line scans of the same location more than once, and uses the phase difference between subsequent line scans at each pixel to calculate flow velocity. In contrast to using the phase derivative in a single scan for velocity calculation, using the phase difference at each pixel between subsequent line scans increases the effective time window by at least two orders of magnitude. For example, for an OCT/ODT image with 100×100 pixels, if the data acquisition time at each pixel is 100 ms, using the phase difference between the subsequent A-line scans increases the time window from 100 $\mu$s to 100×100 $\mu$s=10 ms. Thus, frequency resolution improves from 10 kHz to 100 Hz, and velocity resolution improves from 3 mm/s to 30 $\mu$m/s. In addition, spatial and velocity resolution is decoupled. Because one compares two subsequent line scans at the same location, speckle modulation of the fringe signal cancels each other and will not affect the phase difference calculation. As a consequence, this method minimizes speckle noise. The information carried by the phase can also be used for speckle average in the structural image. In addition, if one introduce a random phase screen in the sampling arm 134 of the interferometer, one can minimize the speckle noise. Furthermore, if one uses phase difference between subsequent frames, the velocity resolution will increase by more than four orders of magnitude. In summary, phase resolved OCT/ODT that uses the phase difference between subsequent line-scans has the following advantages:

1. high velocity sensitivity (a factor of more than 100);
2. high image speed without compromising velocity sensitivity (a factor of more than 100);
3. decouple spatial and velocity resolution;
4. minimize speckle noise;
5. map blood microcirculation with high spatial resolution and high velocity sensitivity; and
6. measure hemodynamics in real time.

There are a number of methods to implement this invention. To demonstrate the principal, we have implemented and tested this invention with a fiber based OCT/ODT described in the previous section in connection with FIG. 7. The speed of the A-line scan is 400 lines/s. After the interference fringe signal $I_k(t)$ is digitized, the complex valued interference fringe function, $\Gamma_{ODT}(t)$, is determined through analytic continuation of the measured interference fringes by a Hilbert transformation. $\Gamma_{ODT}(t)$ can be written as $$\Gamma_{ODT}(t) = I_k(t) + i\, Q_k(t)$$

with $I_k(t)$ representing the real part and $Q_k(t)$ the imaginary part of $\Gamma_{ODT}(t)$ in I-th A-line scan. $Q_k(t)$ is related to $I_k(t)$ by a Hilbert transform given in equation 1 above. If we scan the A-line at same location multiple times, the phase of the fringes of these A-line scans can be used to calculate the average phase change between subsequent A-line scans. The mean angular frequency of such a phase shift, which is actually the Doppler shift, can be calculated by equation 2 above. In addition, the standard deviation of the Doppler spectrum can be calculated by: equation 3 above. The Doppler standard deviation image can be used to identified flow location and as well as indication of turbulence.

The device has been used to image the microcirculation in rodent and human skin. Doppler shifts as small as 30 Hz have been measured with an A-line scan speed of 400 Hz. As a consequence, the microvasculature of a port wine stain patient can be measured. This technology can be used for monitoring and feed back control of laser treatment of port wine stain patients, determination of burn depth, and feed back control of debridement of burned tissue.

In a second embodiment of FIG. 1 a light source 10 for the interferometer, generally denoted by reference numeral 12, is a broadband 1.3 $\mu$m superluminescent diode from AFC, Inc. (Quebec, Canada). Interferometer 12 is comprised of a fiber optic source arm 11, fiber optic detector arm 13, fiber optic reference arm 15 and fiber optic sample arm 17. The arms of interferometer 12 could also be established in free space or other light conducting paths with appropriate modification. The polarized output power of diode 10 is 5 mW with a bandwidth of 65 nm. In the reference arm 15 of interferometer 12 a rapid-scanning optical delay line 14 is used that employs a grating 16 to control the phase and the group delays separately so that no phase modulation is generated when the group delay is scanned. RSOD 14 includes in addition to grating 16 focussing optics and a reference mirror 19 which is driven or oscillated by a scan driver 21 from Cambridge Technology (Massachusetts). The phase modulation is generated through an electro-optic phase modulator 18 that produces a stable carrier frequency. A digital delay generator 20 from Stanford Research Systems (Stanford, Calif.) is used to synchronize the electro-optic phase modulator 18, an analog-digital converter 22, and an A-scan controller 24. The digitized fringe signal is processed with a computer, generally denoted by reference numeral 26, to generate both structural and Doppler images from complex analytic continuation of the interference fringes. As will be discussed below computer 26 includes a Hilbert transform and digital bandpass filter module 38, a phase analyzing module 40 and an OCT and ODT image display module 42. Modules 38, 40, and 42 include a combination of software and hardware for performing the defined corresponding functions described above.

The optical probe 28 in the sampling arm is comprised of a gradient-index lens 30 (N.A., 0.2) that is placed so that light from the end of the fiber 17 is focused into the sample 34 with a beam size of approximately 10 $\mu$m. The probing beam is aligned at a small angle (50°–100°) with respect to the tissue surface normal so that blood flow parallel to the surface can produce a Doppler frequency shift. Mounting probe 28 upon a voice-coil translation stage 36 (PI, Inc., Waldbronn, Germany), diagrammatically represented in FIG. 1 by a dotted outline, generates a stepped lateral scan for tomographic imaging. At each step in the lateral scan, not less than three and preferably eight A-line scans are recorded at a speed of 400 Hz to increase the signal/noise ratio in the velocity image. The time for acquiring an image with 100×100 pixels is 2 s. The Doppler frequency shift is determined by calculation of the average phase shift between sequential A-line scans.

To remove the baseline phase shift, which is caused by instrument synchronization and possible tissue movement, a reference plane can be introduced to the system. The cover glass and/or tissue surface acts as such a reference plane to remove the phase noise after assuming the phase-shift in the reference plane is equal to zero. The following equation is used to determine the baseline phase noise in the reference plane selected:

$$\phi_n = \tan^{-1}\left(\frac{\text{Im}\left(\sum_{i=1}^{n}(\tilde{\Gamma}(t_i))_j \cdot (\tilde{\Gamma}(t_i))_{j+1}^*\right)}{\text{Re}\left(\sum_{i=1}^{n}(\tilde{\Gamma}(t_i))_j \cdot (\tilde{\Gamma}(t_i))_{j+1}^*\right)}\right)$$

Then the following equation is applied to recalculating the complex signal for all the pixel in a line scan to remove the base line phase shift:

$$\Gamma(t_i)'_{j+l} = \Gamma(t_i)_{j+l} e^{-i\phi_n}$$

To increase the maximum detectable Doppler frequency shift, which is limited by the axial scanning rate, a phase-tracking technique is used. This method is based on the assumption that the Doppler frequency difference between the neighbor pixel is smaller than half of the axial scanning rate. If the calculated value is greater than half of scanning rate, $\pi$ is added to the phase shift value because $\tan(\phi)=\tan(\phi+\pi)$. After applying this technique, the maximum detectable Doppler frequency shift can exceed several times of axial scanning rate. The dynamic range of phase resolved ODT is increased with the phase-tracking technique.

Figure 2C:
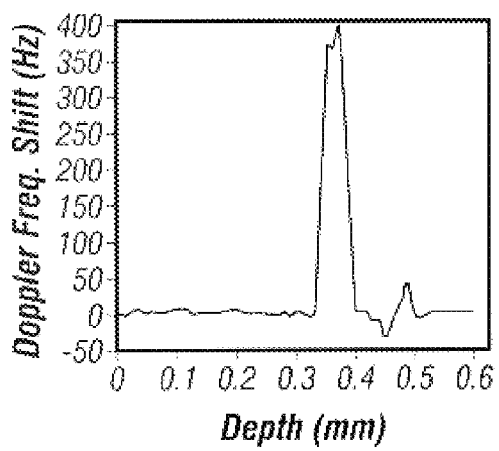
FIGS. 2C and 2D are graphs which show the velocity profile from human skin (finger) corresponding to the images of FIGS. 2A and 2B respectively.
Figure 2D:
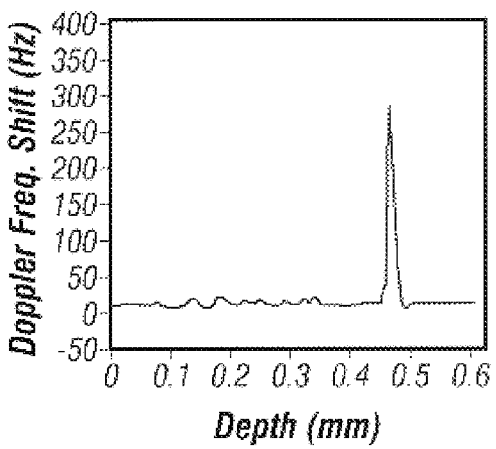

To demonstrate the ability of phase-resolved ODT to image in vivo blood flow, subsurface microcirculation in human skin was imaged. FIG. 2 shows images obtained from the ring finger of a human volunteer. Cross-sectional structural (FIG. 2A) and velocity (FIG. 2B) images are obtained simultaneously. The image size is 200 (lateral) by 200 (axial) pixels with a size of 10 $\mu$m/pixel. The rapid-scanning optical delay scanning rate is 400 Hz, and the electro-optic phase modulators modulation frequency is 800 kHz. The sampling rate of the analog-digital converter is 5 MHz, and the number of data points for each A scan is 4069 for convenient Hilbert transformation. Other parameters could be chosen according to conventional principles. To prevent surface movement the image area was placed in tight contact with a glass window. Index-matching oil was inserted between the glass and the skin to decrease the light reflection from the skin surface. The velocity image is grey scale coded, where white represents the highest absolute velocity of blood flow moving toward the probe and black represents zero velocity. Color coding can also be done where red represents (positive Doppler shift) and blue represents flow in the opposite direction. Pixel intensity represents the absolute velocity. No blood vessels are observed in the structural OCT image in FIG. 2A. One large vein with a diameter of about 60 $\mu$m with positive blood-flow velocity is indicated by arrow 1 in FIG. 2B. Several smaller vessels having a diameter of about 10–30 $\mu$m can be detected at a depth of 300 to 600 $\mu$m. The velocity profile in the axial direction in the center of the vein indicated by arrow 1 in FIG. 2B, is shown in FIG. 2C. The measured Doppler frequency shift in the center of the vein is 400 Hz, which corresponds to a blood-flow velocity of approximately 3.0 mm/s and is in close agreement with known values, assuming that the angle between the direction of blood flow and the optical probe is 85°. The background noise in the velocity image is very small, and velocity sensitivity of the order of 10 $\mu$m/s was achieved in previous experiments with an in vitro tube model. It is important to note that the background noise in some pixels under the large vein is much higher than normal, because when light passes through a vessel containing moving particles, namely red blood cells, some forward scattering will also introduce a Doppler frequency shift. Since forward scattering does not change the optical path length and the Doppler shift is unpredictable, this effect appears as shadowing in the velocity image. The small white dots in the velocity image (FIG. 2B) are believed to be capillaries, because similar structures are observed at exactly the same position in repetitive scans. The velocity profile (FIG. 2D) from one capillary, indicated by arrow 2 in FIG. 2B, shows that the vessel diameter is approximately 20 $\mu$m, which we believe is the smallest vessel ever imaged by ODT.

OCT and ODT images of blood flow taken from the palm of the hand of a human volunteer are shown in FIGS. 3A and B. Two large vessels with blood flow in opposite directions can be seen approximately 1.0 mm below the surface, indicating that phase-resolved OCT/ODT can image blood flow from relatively deep vessels in highly scattering human skin.

In summary, what has been demonstrated is a novel fast scanning phase-resolved OCT/ODT system that can measure blood flow in human skin with high velocity sensitivity. The phase-resolved technique decouples spatial resolution and velocity sensitivity in flow images and increases imaging speed by more than two orders of magnitude without compromising either spatial resolution or velocity sensitivity. The minimum flow velocity that can be detected with an A-line scanning speed of 400 Hz is as low as 10 $\mu$m/s, while a spatial resolution of 10 $\mu$m is maintained. Finally, what is presented here is the first phase-resolved OCT/ODT images of blood flow in human skin.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for phase-resolved optical tomography capable of simultaneously imaging fluid flow and morphology in a sample with fast scanning speed and high velocity sensitivity comprising:

providing a source of at least partially coherent radiation through an interferometer, said at least partially coherent radiation characterized by a phase;

phase modulating said radiation in said interferometer at a modulation frequency;

scanning said sample with said source of at least partially coherent radiation through said interferometer in a sequence of pixel line scans, said sample having a fluid flow therein;

changing said phase of said at least partially coherent radiation in response to said fluid flow at each pixel of each pixel line scan;

detecting interference fringes of said radiation backscattered from said sample into said interferometer;

processing said detected interference fringes to determine ODT phase signals of said detected backscattered interference fringes at each pixel of said pixel line scans to determine said corresponding phase at each pixel in a data window;

comparing said phase between corresponding pixels in two line scans to generate a difference between said phase at said two corresponding pixels in two line scans whereby speckle is substantially reduced; and generating a tomographic image of the fluid flow in said sample from said phase difference at each pixel.

2. The method of claim 1 wherein comparing said phase between corresponding pixels in two line scans comprises comparing said phase between corresponding pixels in two sequential line scans.

3. The method of claim 1 wherein comparing said phase between corresponding pixels in two line scans comprises comparing said phase between corresponding pixels in two sequential scans of a single line.

4. The method of claim 1 wherein said sequence of pixel line scans are scanned in groups of line scans organized into sequential frames, and wherein comparing said phase between corresponding pixels in two line scans comprises comparing said phase between corresponding pixels in two scans of a single line in two sequential frames.

5. The method of claim 1 where processing said detected interference fringes to determine ODT phase signals of said detected backscattered interference fringes comprises determining said ODT phase signals in a computer from a complex function, $\tilde{\Gamma}_{ODT}(t)$, which is determined through analytic continuation of said detected interference fringes function, $\Gamma_{ODT}(t)$, by use of said Hilbert transformations, namely:

$$\tilde{\Gamma}_{ODT}(t) = \Gamma_{ODT}(t) + \frac{i}{\pi} P \int_{-\infty}^{\infty} \frac{\Gamma_{ODT}(\tau)}{\tau - t} d\tau = A(t)\exp[i\varphi(t)]$$

where P denotes the Cauchy principle value and A(t) and $\psi$(t) are the amplitude and the phase of $\Gamma_{ODT}(t)$ respectively.

6. The method of claim 5 where processing said detected interference fringes to determine ODT phase signals of said detected backscattered interference fringes through the use of a Hilbert transformation comprises determining said phase shift, $\Delta\psi$, in said computer at each pixel between sequential line scans by the Doppler frequency shift at each pixel between, $\omega = \Delta\omega/T$ where T is the time interval between successive line scans.

7. The method of claim 1 where processing said detected interference fringes to determine ODT phase signals of said detected backscattered interference fringes comprises determining said ODT phase signals in a computer or digital signal processor by:

applying a first fast Fourier transformation in said computer to said detected interference fringes to produce a transformed signal;

passing said transformed signal through a digital filter in said computer to reduce noise to produce a filtered signal;

multiplying said filtered signal by the Heaviside function, H($\omega$) in said computer to produce a multiplied signal; and applying a second fast Fourier transformation in said computer to said multiplied signal to producer $\Gamma_{ODT}(t)$; and extracting in said computer said ODT phase signals from $\Gamma_{ODT}(t)$.

8. The method of claim 1 wherein said interferometer has a reference arm, a sample arm and a detection arm and further comprising prior to detecting interference fringes of said radiation backscattered from said sample into said interferometer:

providing circularly polarized reflected radiation from said reference arm;

providing linearly polarized reflected radiation from said sample arm;

combining said circularly polarized reflected radiation from said reference arm and said linearly polarized reflected radiation from said sample arm in a coupler; and splitting radiation from said coupler into two polarized beams in said detection arm with a polarizing beam splitter with an axis of polarization set at 45° to said linearly polarized reflected radiation from said sample arm, wherein detecting interference fringes comprises detecting said two polarized beams in two corresponding detectors to generate two corresponding signals comprising in turn the real and imaginary parts of $\Gamma_{ODT}(t)$ so that said phase is directly measured.

9. The method of claim 1 where generating said tomographic image of the fluid flow in said sample comprises generating a structural image of said sample.

10. The method of claim 1 where generating said tomographic image of the fluid flow in said sample comprises generating a velocity image of fluid in said sample.

11. The method of claim 1 further comprising determining a phase shift $\Delta f = \Delta \psi / T$ from an average Doppler frequency shift, $<\Delta f>$, between sequential line scans using the equation:

$$\langle \Delta f \rangle = \frac{1}{2\pi T} \tan^{-1} \left( \frac{\operatorname{Im}\left( \sum_{j=1}^{n} \tilde{\Gamma}_j \cdot \tilde{\Gamma}_{j+1}^* \right)}{\operatorname{Re}\left( \sum_{j=1}^{n} \tilde{\Gamma}_j \cdot \tilde{\Gamma}_{j+1}^* \right)} \right)$$

where T is the time interval between sequential scans, and n is the number of sequential scans averaged.

12. The method of claim 11 where determining a phase shift from an average Doppler frequency shift between sequential line scans comprises averaging at least three sequential line scans to increase the signal-to-noise ratio in images.

13. The method of claim 1 further comprising determining a standard deviation of a Doppler power spectrum and generating said tomographic image of the fluid flow in said sample from said standard deviation of said Doppler power spectrum.

14. The method of claim 13 where determining said standard deviation of a Doppler power spectrum comprises determining said standard deviation from the equation:

$$\sigma^2 = \frac{\int_{-\infty}^{\infty} (\omega - \overline{\omega})^2 P(\omega) d\omega}{\int_{-\infty}^{\infty} P(\omega) d\omega} = \frac{1}{T^2}\left(1 - \frac{\left|\sum_{j=1}^{n} \tilde{\Gamma}_j \cdot \tilde{\Gamma}_{j+1}^*\right|}{\sum_{j=1}^{n} \tilde{\Gamma}_j \cdot \tilde{\Gamma}_j^*}\right)$$

where T is the time interval between sequential scans, $P(\omega)$ is said Doppler power spectrum, and $\overline{\omega}$ is the centroid value of a Doppler frequency shift.

15. The method of claim 1 where generating said corresponding phase at each pixel in a data window comprises extracting said phase shift by electronic demodulation of said detected interference fringes.

16. The method of claim 1 where said scanning is characterized by a scanning rate, and adding $\pi$ to said phase difference because $\tan(\phi)=\tan(\phi+\pi)$, when a Doppler frequency difference related to said phase difference is greater than half of said scanning rate so that said Doppler frequency difference can exceed said scanning rate.

17. A method for phase-resolved optical tomography comprising:

providing a source of at least partially coherent radiation through an interferometer, said at least partially coherent radiation characterized by a phase;

phase modulating said radiation in said interferometer at a modulation frequency;

scanning said sample with said source of at least partially coherent radiation through said interferometer in a sequence of pixel line scans, said sample having a fluid flow therein;

changing said phase of said at least partially coherent radiation in response to said fluid flow at each pixel of each pixel line scan;

detecting interference fringes of said radiation backscattered from said sample into said interferometer;

processing said detected interference fringes to determine ODT phase signals of said detected backscattered interference fringes at each pixel of said pixel line scans to generate a corresponding rate of change of said phase at each pixel in a data window through the use of a Hilbert transformation at each pixel, and generating a tomographic image of the fluid flow in said sample from said rate of change of said phase at each pixel.

18. A method for phase-resolved optical tomography comprising:

providing a source of at least partially coherent radiation through an interferometer with a reference arm, a sample arm and a detection arm, said at least partially coherent radiation characterized by a phase;

phase modulating said radiation in said interferometer at a modulation frequency;

scanning said sample with said source of at least partially coherent radiation through said interferometer in a sequence of pixel line scans, said sample having a fluid flow therein so that said phase of said at least partially coherent radiation is changed in response to said fluid flow at each pixel of each pixel line scan;

providing circularly polarized reflected radiation from said reference arm;

providing linearly polarized reflected radiation from said sample arm;

combining said circularly polarized reflected radiation from said reference arm and said linearly polarized reflected radiation from said sample arm in a coupler; and splitting radiation from said coupler into two polarized beams in said detection arm with a polarizing beam splitter with an axis of polarization set at 45° to said linearly polarized reflected radiation from said sample arm, detecting interference fringes of said radiation backscattered from said sample into said interferometer in said two polarized beams in two corresponding detectors to generate two corresponding signals comprising in turn the real and imaginary parts of $\Gamma_{ODT}(t)$ so that said phase is directly measured; and generating a tomographic image of the fluid flow in said sample from said phase at each pixel.

19. An apparatus for phase-resolved optical tomography capable of simultaneously imaging fluid flow and morphology in sample with fast scanning speed and high velocity sensitivity comprising:

an interferometer;

a source of at least partially coherent radiation through coupled to said interferometer, said at least partially coherent radiation characterized by a phase;

phase modulator coupled to said source to modulate said radiation in said interferometer at a modulation frequency;

a scanner for scanning said sample with said source of at least partially coherent radiation through said interferometer in a sequence of pixel line scans, said sample having a fluid flow therein so that said phase of said at least partially coherent radiation is changed in response to said fluid flow at each pixel of each pixel line scan;

a detector to detect interference fringes of said radiation backscattered from said sample into said interferometer;

a processor to determine said corresponding phase at each pixel of said pixel line scans from said ODT phase signals of said detected backscattered interference fringes and to compare said phase between corresponding pixels in two line scans to generate a difference between said phase at said two corresponding pixels in two line scans whereby speckle is substantially reduced; and a display to generate a tomographic image of the fluid flow in said sample from said difference at each pixel.

20. The apparatus of claim 19 wherein said processor compares said phase between corresponding pixels in two sequential line scans.

21. The apparatus of claim 19 wherein said processor compares said phase between corresponding pixels in two sequential scans of a single line.

22. The apparatus of claim 19 wherein said sequence of pixel line scans are scanned in groups of line scans organized into sequential frames, and wherein said processor compares said phase between corresponding pixels in two scans of a single line in two sequential frames.

23. The apparatus of claim 19 where processor determines said ODT phase signals from a complex function, $\tilde{\Gamma}_{ODT}(t)$, which. is determined through analytic continuation of said detected interference fringes function, $\Gamma_{ODT}(t)$, by use of said Hilbert transformations, namely:

$$\tilde{\Gamma}_{ODT}(t) = \Gamma_{ODT}(t) + \frac{i}{\pi} P \int_{-\infty}^{\infty} \frac{\Gamma_{ODT}(\tau)}{\tau - t} d\tau = A(t)\exp[i\varphi(t)]$$

where P denotes the Cauchy principle value and A(t) and ψ(t) are the amplitude and the phase of $\tilde{\Gamma}_{ODT}(t)$ respectively.

24. The apparatus of claim 19 where said display for generating said tomographic image of the fluid flow in said sample comprises generates a velocity image of said sample.

25. The apparatus of claim 19 where said processor determines a phase shift Δf=Δψ/T from an average Doppler frequency shift, <Δf>, between sequential line scans using the equation:

$$\langle \Delta f \rangle = \frac{1}{2\pi T} \tan^{-1} \left( \frac{\text{Im}\left(\sum_{j=1}^{n} \tilde{\Gamma}_j \cdot \tilde{\Gamma}_{j+1}^*\right)}{\text{Re}\left(\sum_{j=1}^{n} \tilde{\Gamma}_j \cdot \tilde{\Gamma}_{j+1}^*\right)} \right)$$

where T is the time interval between sequential scans, and n is the number of sequential scans averaged.

26. The apparatus of claim 25 where said processor determines a phase shift from an average Doppler frequency shift between sequential line scans comprises averaging at least three sequential line scans to increase the signal-to-noise ratio in images.

27. The apparatus of claim 19 where said processor determines a standard deviation of a Doppler power spectrum and said display generates said tomographic image of the fluid flow in said sample from said standard deviation of said Doppler power spectrum.

28. The apparatus of claim 27 where said processor determines said standard deviation of a Doppler power spectrum comprises determining said standard deviation from the equation:

$$\sigma^2 = \frac{\int_{-\infty}^{\infty} (\omega - \overline{\omega})^2 P(\omega) d\omega}{\int_{-\infty}^{\infty} P(\omega) d\omega} = \frac{1}{T^2}\left(1 - \frac{\left|\sum_{j=1}^{n} \tilde{\Gamma}_j \cdot \tilde{\Gamma}_{j+1}^*\right|}{\sum_{j=1}^{n} \tilde{\Gamma}_j \cdot \tilde{\Gamma}_j^*}\right)$$

where T is the time interval between sequential scans, P(ω) is said Doppler power spectrum, and $\overline{\omega}$ is the centroid value of a Doppler frequency shift.

29. The apparatus of claim 19 where said processor determines said corresponding phase at each pixel in a data window by extracting said phase by electronic demodulation of said detected interference fringes.

30. The apparatus of claim 19 where said scanner is characterized by a scanning rate, and wherein said processor adds π to said phase difference when a Doppler frequency difference related to said phase difference is greater than half of said scanning rate, because tan(φ)=tan(φ+π), so that said Doppler frequency difference can exceed said scanning rate.

31. The apparatus of claim 19 where said processor determines said ODT phase signals of said detected backscattered interference fringes through the use of a Hilbert transformation by determining said phase shift, Δψ, in said computer at each pixel between sequential line scans by the Doppler frequency shift at each pixel between, ω=Δψ/T where T is the time interval between successive line scans.

32. The apparatus of claim 19 where said display for generating said tomographic image of the fluid flow in said sample comprises generates a structural image of said sample.

33. An apparatus for phase-resolved optical tomography of a sample comprising:

an interferometer a source of at least partially coherent radiation coupled to said interferometer, said at least partially coherent radiation characterized by a phase;

a modulator for phase modulating said radiation in said interferometer at a modulation frequency;

a scanner for scanning said sample with said source of at least partially coherent radiation through said interferometer in a sequence of pixel line scans, said sample having a fluid flow therein in which said phase of said at least partially coherent radiation is changed in response to said fluid flow at each pixel of each pixel line scan;

a detector for detecting interference fringes of said radiation backscattered from said sample into said interferometer;

a processor for processing said detected interference fringes to determine ODT phase signals of said detected backscattered interference fringes at each pixel of said pixel line scans to generate a corresponding rate of change of said phase at each pixel in a data window through the use of a Hilbert transformation at each pixel, and a display for generating a tomographic image of the fluid flow in said sample from said rate of change of said phase at each pixel.

34. An apparatus for phase-resolved optical tomography in a sample comprising:

an interferometer with a reference arm, a sample arm and a detection arm;

a source of at least partially coherent radiation coupled to said interferometer, said at least partially coherent radiation characterized by a phase;

a modulator for phase modulating said radiation in said interferometer at a modulation frequency;

a scanner for scanning said sample with said source of at least partially coherent radiation through said interferometer in a sequence of pixel line scans, said sample having a fluid flow therein so that said phase of said at least partially coherent radiation is changed in response to said fluid flow at each pixel of each pixel line scan;

a circular polarizer for circularly polarizing reflected radiation from said reference arm;

a linear polarizer for linearly polarized reflected radiation from said sample arm;

a coupler for combining said circularly polarized reflected radiation from said reference arm and said linearly polarized reflected radiation from said sample arm; and a beam splitter for splitting radiation from said coupler into two polarized beams in said detection arm with a polarizing beam splitter with an axis of polarization set at 45° to said linearly polarized reflected radiation from said sample arm, two corresponding detectors for detecting interference fringes of said radiation backscattered from said sample into said interferometer in said two polarized beams to generate two corresponding signals comprising in turn the real and imaginary parts of $\Gamma_{ODT}(t)$ so that said phase is directly measured; and a display for generating a tomographic image of the fluid flow in said sample from said phase at each pixel.

35. A method for optical tomography comprising:

providing a source of at least partially coherent radiation through an interferometer, said at least partially coherent radiation characterized by a phase;

providing a rapid-scanning optical delay line and an electro-optic modulator coupled to said rapid-scanning optical delay line;

phase modulating said radiation in said interferometer by means of said rapid-scanning optical delay line and electro-optic modulator in combination at a modulation frequency with a stable phase modulation;

scanning said sample with said source of at least partially coherent radiation through said interferometer;

detecting interference fringes of said radiation backscattered from said sample into said interferometer.

36. The method of claim 35 further comprising operating said rapid-scanning optical delay line at a zero carrier frequency.

37. The method of claim 35 where phase modulating said radiation in said interferometer comprises phase modulating said radiation in a reference arm of said interferometer.

38. The method of claim 35 where said optical tomography is phase-resolved optical tomography capable of simultaneously imaging fluid flow and morphology in a sample with fast scanning speed and high velocity sensitivity, where phase modulating said radiation in said interferometer phase modulates said radiation with a stable phase modulation which is repeatable between multiple scans of said sequence of pixel line scans, where scanning said sample scans said sample in a sequence of pixel line scans, said sample having a fluid flow therein; and further comprising:

changing said phase of said at least partially coherent radiation in response to said fluid flow at each pixel of each pixel line scan;

processing said detected interference fringes to determine ODT phase signals of said detected backscattered interference fringes at each pixel of said pixel line scans to determine said corresponding phase at each pixel in a data window;

comparing said phase between corresponding pixels in two line scans to generate a difference between said phase at said two corresponding pixels in two line scans whereby speckle is substantially reduced; and generating a tomographic image of the fluid flow in said sample from said phase difference at each pixel.

39. An apparatus for optical tomography comprising:

an interferometer;

a source of at least partially coherent radiation coupled to said interferometer, said at least partially coherent radiation characterized by a phase;

a rapid-scanning optical delay line;

an electro-optic modulator coupled to said rapid-scanning optical delay line to modulate said radiation in said interferometer at a modulation frequency with a stable phase modulation;

a scanner for scanning said sample with said source of at least partially coherent radiation through said interferometer; and a detector to detect interference fringes of said radiation backscattered from said sample into said interferometer.

40. The apparatus of claim 39 where said rapid-scanning optical delay line operates at a zero carrier frequency.

41. The apparatus of claim 39 where said interferometer has a reference arm and where said rapid-scanning optical delay line and electro-optic modulator are disposed in said reference arm of said interferometer.

42. The apparatus of claim 39 where said optical tomography is phase-resolved optical tomography capable of simultaneously imaging fluid flow and morphology in sample with fast scanning speed and high velocity sensitivity, where said rapid-scanning optical delay line and electro-optic modulator phase modulator in combination modulate said radiation in said interferometer at a modulation frequency in which said radiation is phase modulated with a stable phase modulation which is repeatable between multiple scans of a sequence of pixel line scans, where said scanner scans said sequence of pixel line scans, said sample having a fluid flow therein so that said phase of said at least partially coherent radiation is changed in response to said fluid flow at each pixel of each pixel line scan, and further comprising:

a processor to determine said corresponding phase at each pixel of said pixel line scans from said ODT phase signals of said detected backscattered interference fringes and to compare said phase between corresponding pixels in two line scans to generate a difference between said phase at said two corresponding pixels in two line scans whereby speckle is substantially reduced; and a display to generate a tomographic image of the fluid flow in said sample from said difference at each pixel.

* * * * *